(12) United States Patent
Hardie et al.

(10) Patent No.: US 12,403,047 B2
(45) Date of Patent: *Sep. 2, 2025

(54) DISPOSABLE ABSORBENT ARTICLES INCLUDING A FIRST ABSORBENT LAYER AND A SECOND ABSORBENT LAYER

(71) Applicant: The Procter & Gamble Company, Cincinnati, OH (US)

(72) Inventors: Stephen Lebeuf Hardie, Mason, OH (US); Joshua Andrew Williams, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/734,121

(22) Filed: Jun. 5, 2024

(65) Prior Publication Data

US 2024/0315887 A1    Sep. 26, 2024

Related U.S. Application Data

(63) Continuation of application No. 16/381,251, filed on Apr. 11, 2019, now Pat. No. 12,036,104.

(Continued)

(51) Int. Cl.
*A61F 13/535* (2006.01)
*A61F 13/15* (2006.01)
(Continued)

(52) U.S. Cl.
CPC ...... *A61F 13/535* (2013.01); *A61F 13/15203* (2013.01); *A61F 13/15658* (2013.01);
(Continued)

(58) Field of Classification Search
None
See application file for complete search history.

(56) References Cited

U.S. PATENT DOCUMENTS

| 1,946,626 A | 2/1934 | Jurgensen |
| 2,296,341 A | 9/1942 | Fourness |

(Continued)

FOREIGN PATENT DOCUMENTS

| CN | 1371671 A | 10/2002 |
| CN | 1612803 A | 5/2005 |

(Continued)

OTHER PUBLICATIONS

Extended EP Search Report and Opinion for Application No. 24192797.9; dated Oct. 17, 2024, 10 pages.

(Continued)

*Primary Examiner* — Michele Kidwell
(74) *Attorney, Agent, or Firm* — Sarah M. DeCristofaro

(57) ABSTRACT

A disposable absorbent article having a longitudinal centerline and a lateral centerline generally perpendicular to the longitudinal centerline is described herein. The disposable absorbent article has a topsheet; a backsheet; and an absorbent system disposed between the topsheet and the backsheet. The absorbent system has a first and second absorbent core configured such that there is an overlap between the first and second absorbent core and a pair of outboard distances for the first and second absorbent cores.

20 Claims, 22 Drawing Sheets

Related U.S. Application Data

(60) Provisional application No. 62/655,959, filed on Apr. 11, 2018.

(51) Int. Cl.
| | | |
|---|---|---|
| *A61F 13/511* | (2006.01) | |
| *A61F 13/514* | (2006.01) | |
| *A61F 13/53* | (2006.01) | |
| *A61F 13/534* | (2006.01) | |
| *A61L 15/60* | (2006.01) | |
| A61F 13/475 | (2006.01) | |
| A61F 13/494 | (2006.01) | |

(52) U.S. Cl.
CPC .......... *A61F 13/511* (2013.01); *A61F 13/514* (2013.01); *A61F 13/534* (2013.01); *A61L 15/60* (2013.01); *A61F 2013/15373* (2013.01); *A61F 2013/15569* (2013.01); *A61F 13/475* (2013.01); *A61F 13/494* (2013.01); *A61F 2013/53024* (2013.01); *A61F 2013/530481* (2013.01); *A61F 2013/530868* (2013.01); *A61F 2013/530927* (2013.01)

(56) References Cited

U.S. PATENT DOCUMENTS

| | | |
|---|---|---|
| 2,929,379 A | 3/1960 | Vita |
| 3,386,442 A | 6/1968 | Reinhardt |
| 3,406,688 A | 10/1968 | Cubitt |
| 3,431,911 A | 3/1969 | Meisel, Jr. |
| 3,528,421 A | 9/1970 | Vaillancourt |
| 3,572,342 A | 3/1971 | Lindquist |
| 3,604,422 A | 9/1971 | Sabee |
| 3,651,809 A | 3/1972 | Champaigne, Jr. |
| 3,695,269 A | 10/1972 | Malaney |
| 3,799,167 A | 3/1974 | Miller et al. |
| 3,805,790 A | 4/1974 | Kaczmarzyk |
| 3,815,602 A | 6/1974 | Johns et al. |
| 3,825,006 A | 7/1974 | Ralph |
| 3,838,693 A | 10/1974 | Sherman |
| 3,871,037 A | 3/1975 | Willington |
| 3,871,378 A | 3/1975 | Duncan et al. |
| 3,878,283 A | 4/1975 | Jones, Sr. |
| 3,954,721 A | 5/1976 | Gross |
| 3,983,095 A | 9/1976 | Bashaw et al. |
| 3,996,936 A | 12/1976 | Widlund et al. |
| 4,047,531 A | 9/1977 | Karami |
| 4,102,340 A | 7/1978 | Mesek et al. |
| 4,136,697 A | 1/1979 | Smith |
| 4,211,227 A | 7/1980 | Anderson et al. |
| 4,231,357 A | 11/1980 | Hessner |
| 4,269,188 A | 5/1981 | Nishizawa et al. |
| 4,285,342 A | 8/1981 | Mesek |
| 4,333,464 A | 6/1982 | Nakano |
| 4,333,465 A | 6/1982 | Wiegner |
| 4,335,722 A | 6/1982 | Jackson |
| 4,338,371 A | 7/1982 | Dawn et al. |
| 4,354,901 A | 10/1982 | Kopolow |
| 4,364,992 A | 12/1982 | Jto et al. |
| 4,381,783 A | 5/1983 | Elias |
| 4,397,644 A | 8/1983 | Matthews et al. |
| 4,410,324 A | 10/1983 | Sabee |
| 4,411,660 A | 10/1983 | Dawn et al. |
| 4,480,000 A | 10/1984 | Hirt et al. |
| 4,500,315 A | 2/1985 | Iskra |
| 4,536,181 A | 8/1985 | Cook |
| 4,537,590 A | 8/1985 | Iskra |
| 4,557,777 A | 12/1985 | Sabee |
| 4,560,372 A | 12/1985 | Pieniak |
| 4,560,379 A | 12/1985 | Stemmler |
| 4,610,678 A | 9/1986 | Weisman |
| 4,655,757 A | 4/1987 | Mcfarland |
| 4,666,439 A | 5/1987 | Williams |
| 4,673,402 A | 6/1987 | Weisman et al. |
| 4,676,784 A | 6/1987 | Erdman |
| 4,685,914 A | 8/1987 | Holtman |
| 4,699,823 A | 10/1987 | Kellenberger |
| 4,710,187 A | 12/1987 | Boland |
| 4,762,521 A | 8/1988 | Roessler et al. |
| 4,770,656 A | 9/1988 | Proxmire |
| 4,781,711 A | 11/1988 | Houghton |
| 4,790,839 A | 12/1988 | Ahr |
| 4,798,603 A | 1/1989 | Meyer |
| 4,806,408 A | 2/1989 | Pierre et al. |
| 4,828,555 A | 5/1989 | Hermansson |
| 4,888,093 A | 12/1989 | Dean |
| 4,888,238 A | 12/1989 | Katz |
| 4,900,318 A | 2/1990 | Toth |
| 4,908,026 A | 3/1990 | Becker et al. |
| 4,911,700 A | 3/1990 | Makoui |
| 4,923,454 A | 5/1990 | Seymour |
| 4,935,022 A | 6/1990 | Lash et al. |
| 4,938,756 A | 7/1990 | Salek |
| 4,944,735 A | 7/1990 | Mokry |
| 4,973,325 A | 11/1990 | Sherrod et al. |
| 4,988,344 A | 1/1991 | Reising et al. |
| 4,988,345 A | 1/1991 | Reising |
| 4,990,147 A | 2/1991 | Freeland |
| 5,009,650 A | 4/1991 | Bernardin |
| 5,013,309 A | 5/1991 | Baigas, Jr. et al. |
| 5,037,409 A | 8/1991 | Wisneski |
| 5,057,096 A | 10/1991 | Faglione |
| 5,061,259 A | 10/1991 | Goldman |
| 5,061,260 A | 10/1991 | Callahan |
| 5,069,676 A | 12/1991 | Ito |
| 5,079,004 A | 1/1992 | Blank |
| 5,087,506 A | 2/1992 | Palumbo |
| 5,098,422 A | 3/1992 | Davis |
| 5,134,007 A | 7/1992 | Mesek et al. |
| 5,147,343 A | 9/1992 | Kellenberger |
| 5,147,345 A | 9/1992 | Lavon |
| 5,149,335 A | 9/1992 | Kellenberger |
| 5,176,668 A | 1/1993 | Bernardin |
| 5,192,606 A | 3/1993 | Proxmire |
| 5,294,478 A | 3/1994 | Wanek et al. |
| 5,300,053 A | 4/1994 | Genaro |
| 5,300,054 A | 4/1994 | Feist |
| 5,304,161 A | 4/1994 | Noel et al. |
| 5,387,207 A | 2/1995 | Dyer |
| 5,411,497 A | 5/1995 | Tanzer |
| 5,425,725 A | 6/1995 | Tanzer |
| 5,433,715 A | 7/1995 | Tanzer |
| 5,440,061 A | 8/1995 | Gibson |
| 5,454,800 A | 10/1995 | Hirt et al. |
| 5,466,513 A | 11/1995 | Wanek |
| 5,509,915 A | 4/1996 | Hanson |
| 5,830,202 A | 11/1998 | Bogdanski et al. |
| 5,853,402 A | 12/1998 | Faulks |
| 5,910,137 A | 6/1999 | Clark et al. |
| 6,068,620 A | 5/2000 | Chmielewski et al. |
| 6,114,597 A | 9/2000 | Romare |
| 6,258,996 B1 | 7/2001 | Goldman |
| 6,280,427 B1 | 8/2001 | Maggiulli |
| 6,319,238 B1 | 11/2001 | Sartorio et al. |
| 6,652,498 B1 | 11/2003 | Glasgow et al. |
| 6,740,069 B2 | 5/2004 | Drevik |
| 7,278,988 B2 * | 10/2007 | Molas ............... A61F 13/47254 604/385.01 |
| 7,686,792 B2 | 3/2010 | Bell et al. |
| 7,744,576 B2 | 6/2010 | Busam |
| 9,238,089 B2 | 1/2016 | Chmielewski et al. |
| 9,308,135 B2 | 4/2016 | You |
| 10,471,620 B2 | 11/2019 | Bittner |
| 10,807,263 B2 | 10/2020 | Busch et al. |
| 11,129,755 B2 * | 9/2021 | Hardie .................... A61F 13/47 |
| 11,324,642 B2 | 5/2022 | Busch et al. |
| 12,036,104 B2 * | 7/2024 | Hardie .................... A61L 15/60 |
| 2003/0225384 A1 | 12/2003 | Zenker et al. |
| 2004/0015142 A1 | 1/2004 | Johnston et al. |
| 2004/0033750 A1 * | 2/2004 | Everett ............ A61F 13/15203 604/378 |
| 2006/0018415 A1 | 1/2006 | Jung |
| 2006/0069367 A1 | 3/2006 | Widlund et al. |

(56) References Cited

U.S. PATENT DOCUMENTS

| | | |
|---|---|---|
| 2009/0036854 A1 | 2/2009 | Guidotti et al. |
| 2011/0004179 A1* | 1/2011 | Kurihara ............... A61F 13/474 |
| | | 604/385.03 |
| 2011/0319848 A1 | 12/2011 | Mckiernan |
| 2012/0043244 A1 | 2/2012 | Hagner |
| 2012/0053547 A1 | 3/2012 | Schroeder |
| 2014/0005623 A1 | 1/2014 | Wirtz et al. |
| 2014/0163500 A1 | 6/2014 | Roe |
| 2014/0213997 A1 | 7/2014 | Tsang |
| 2015/0173971 A1 | 6/2015 | Johansson et al. |
| 2016/0235602 A1 | 8/2016 | Johns et al. |
| 2017/0312146 A1 | 11/2017 | Bianchi |
| 2018/0098890 A1 | 4/2018 | Hardie et al. |
| 2018/0098891 A1 | 4/2018 | Hardie et al. |
| 2018/0098893 A1 | 4/2018 | Viens |
| 2019/0314211 A1 | 10/2019 | Busch et al. |
| 2019/0314212 A1 | 10/2019 | Busch et al. |
| 2019/0314219 A1 | 10/2019 | Hardie et al. |
| 2019/0314220 A1 | 10/2019 | Hardie et al. |
| 2021/0378882 A1 | 12/2021 | Hardie et al. |

FOREIGN PATENT DOCUMENTS

| | | | |
|---|---|---|---|
| CN | 203417296 U | 2/2014 | |
| EP | 0631768 A1 | 1/1995 | |
| EP | 2594238 A2 | 5/2013 | |
| EP | 2901992 B1 | 12/2016 | |
| EP | 3205318 A1 | 8/2017 | |
| GB | 125865 A | 5/1919 | |
| GB | 1259865 A | 1/1972 | |
| GB | 1259896 A | 1/1972 | |
| GB | 2304586 * | 3/1997 | ............ A61F 13/15 |
| WO | 9962801 A2 | 12/1999 | |
| WO | 0076447 A1 | 12/2000 | |
| WO | 2005060892 A1 | 7/2005 | |
| WO | 2013180937 A1 | 12/2013 | |
| WO | 2014145804 A1 | 9/2014 | |
| WO | 2015188032 A1 | 12/2015 | |
| WO | 2016195632 A1 | 12/2016 | |

OTHER PUBLICATIONS

PCT Search Report and Written Opinion for PCT/US2019/026935 dated Jul. 4, 2019, 16 pages.
All Office Actions, U.S. Appl. No. 16/381,251, filed Apr. 11, 2019.
All Office Actions, U.S. Appl. No. 16/381,084, filed Apr. 11, 2019.
All Office Actions, U.S. Appl. No. 16/381,662, filed Apr. 11, 2019.
All Office Actions; U.S. Appl. No. 16/381,075, filed Apr. 11, 2019.

* cited by examiner

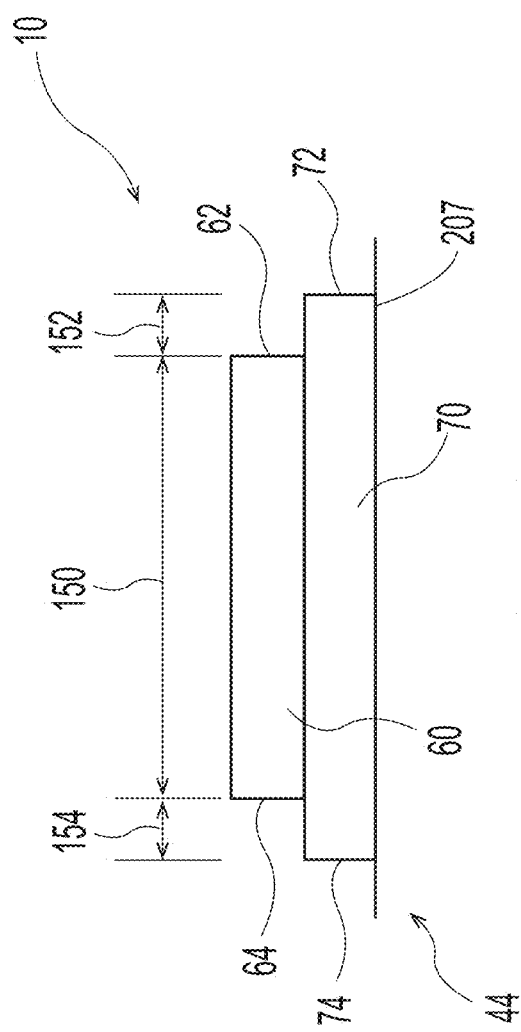

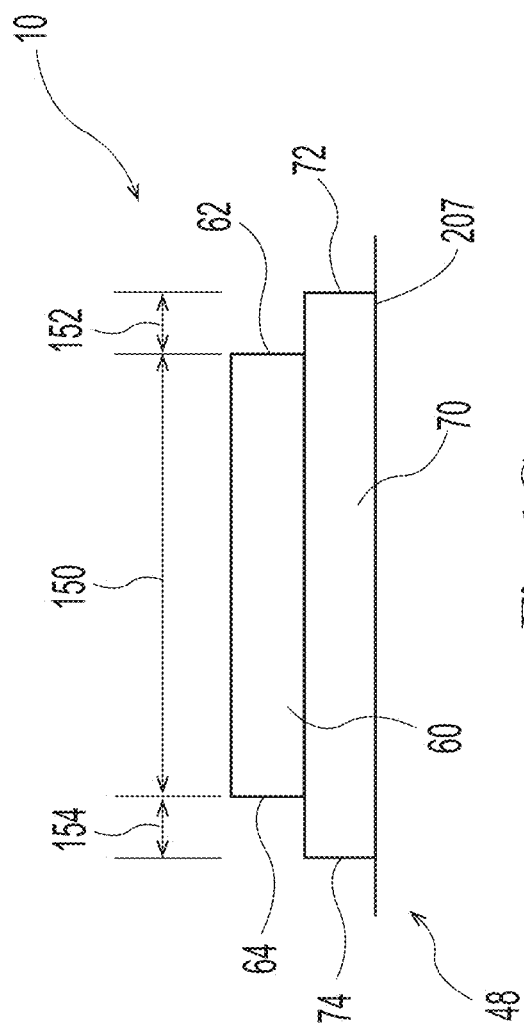

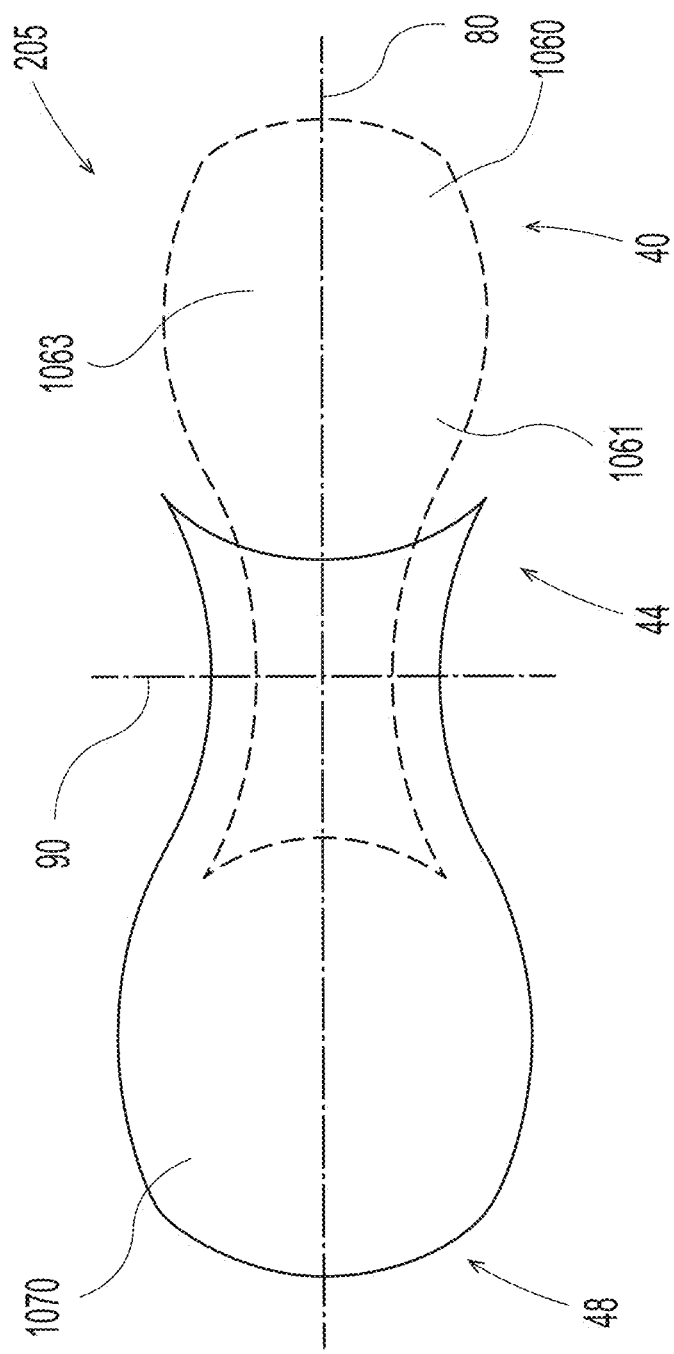

DISPOSABLE ABSORBENT ARTICLES INCLUDING A FIRST ABSORBENT LAYER AND A SECOND ABSORBENT LAYER

CROSS REFERENCE TO RELATED APPLICATION

This application is a continuation of U.S. patent application Ser. No. 16/381,251 filed on Apr. 11, 2019, which claims the benefit, under 35 U.S.C. § 119(e), of U.S. Provisional Patent Application Ser. No. 62/655,959 filed on Apr. 11, 2018, the entire disclosures of all of which are fully incorporated by reference herein.

FIELD OF THE INVENTION

The present invention pertains to disposable absorbent articles suitable for absorbing and containing body exudates.

BACKGROUND OF THE INVENTION

A variety of disposable absorbent articles have been relied on by consumers to handle or manage body exudates. These consumers may include babies, toddlers, children, teenagers, adults, and elderly persons. Thus, it is clear that the types of fluids or body exudates managed by such articles may vary as well to include urine, feces, menses, and other discharges. Typically, in the case of adults, the articles take the form of sanitary napkins, adult incontinence pads, and adult incontinence diapers or undergarments. One of the primary drivers of the desirability of these products to wearers is to give them assurance that when they experience incontinence, the occurrence of such will go unnoticed by others and even more ideally by the wearers.

One way of improving the performance and overall discretion of disposable absorbent articles that has been widely utilized by manufacturers has been the inclusion of superabsorbent polymers which are able to intake increased amounts of liquid and consequently form a swollen hydrogel material. The resulting hydrogel serves to retain fluid such as discharged body liquids within the structure. An absorbent structure of this type wherein hydrogel-forming materials in particulate form are incorporated into fibrous webs is disclosed in Weisman and Goldman; U.S. Pat. No. 4,610,678; issued Sep. 9, 1986.

While disposable absorbent articles with these superabsorbent materials tend to be highly absorbent and less bulky, there are a number of users of these products that have a high body mass index (BMI) for which these products still leave much to be desired. In particular, these users tend to experience exaggerated bunching of the absorbent article during wear and as a result there can be increased opportunity for leaks to occur.

Consequently, there is a need for a disposable absorbent article which targets to provide increased protection from leakage to consumers which have a high BMI while maintaining a level of discretion to the wearer while in use.

SUMMARY OF THE INVENTION

Described herein are disposable absorbent articles that can provide improved protection from leakage to consumers with a wide variety of BMI's. Additionally, processes disclosed herein can facilitate manufacturing of such articles.

In some embodiments, an absorbent article comprises: a longitudinal centerline and a lateral centerline generally perpendicular to the longitudinal centerline, the disposable absorbent article further comprising: a topsheet; a backsheet; a first end region an opposing second end region, and an intermediate region disposed between the first end region and the second end region; a first absorbent core disposed between the topsheet and the backsheet, the first absorbent core having an intermediate region first absorbent core width; a second absorbent core disposed between the first absorbent core and the backsheet, the second absorbent core, wherein the second absorbent core has an intermediate region second absorbent core width, and wherein the intermediate region first absorbent core width is greater than the intermediate region second absorbent core width or the intermediate region second absorbent core width is greater than the intermediate region first absorbent core width by an intermediate outboard distance, wherein first absorbent core and the second absorbent core overlap by an overlap distance, and wherein the first absorbent core and the second absorbent core are disposed in a longitudinally offset configuration.

In some embodiments, a sanitary napkin has a longitudinal centerline and a lateral centerline generally perpendicular to the longitudinal centerline. The sanitary napkin may comprise: a topsheet; a backsheet; a first end region, an opposing second end region and an intermediate region disposed between the first end region and the second end region; a first absorbent layer disposed between the topsheet and the backsheet, the first absorbent layer having a first end region first absorbent layer width, an intermediate region first absorbent layer width measured along the lateral centerline, and a second end region first absorbent layer width; a second absorbent layer disposed between the first absorbent layer and the backsheet, the second absorbent layer having a first end region second absorbent layer width, an intermediate region second absorbent layer width measured along the lateral centerline, and a second end region second absorbent layer width, wherein the respective widths have the following relationships: the first end region first absorbent layer width is greater than the second end region first absorbent layer width, and the second end region first absorbent layer width is greater than the intermediate region first absorbent layer width, and the first end region second absorbent layer width is greater than the second end region second absorbent layer width, and the second end region second absorbent layer width is greater than the intermediate region second absorbent layer width, wherein the first absorbent layer comprises a first end edge and an opposing second end edge, wherein the second absorbent layer comprises a first end edge and an opposing second end edge, and wherein the first end edge of the first absorbent layer is coterminous with the first end edge of the second absorbent layer or the second end edge of the first absorbent layer is coterminous with the second end edge of the second absorbent layer.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

FIG. 1F is a representation of a cross section of the article of FIG. 1A in an intermediate region along line 1F-1F;

FIG. 1G is a representation of a cross section of the article of FIG. 1A in a second end region along line 1G-1G;

FIG. 1I shows an alternative configuration of an absorbent system which can be utilized in the absorbent article of the present disclosure;

FIG. 10 is a representation of another absorbent article constructed in accordance with the present disclosure.

DETAILED DESCRIPTION OF THE INVENTION

Figure 1A:
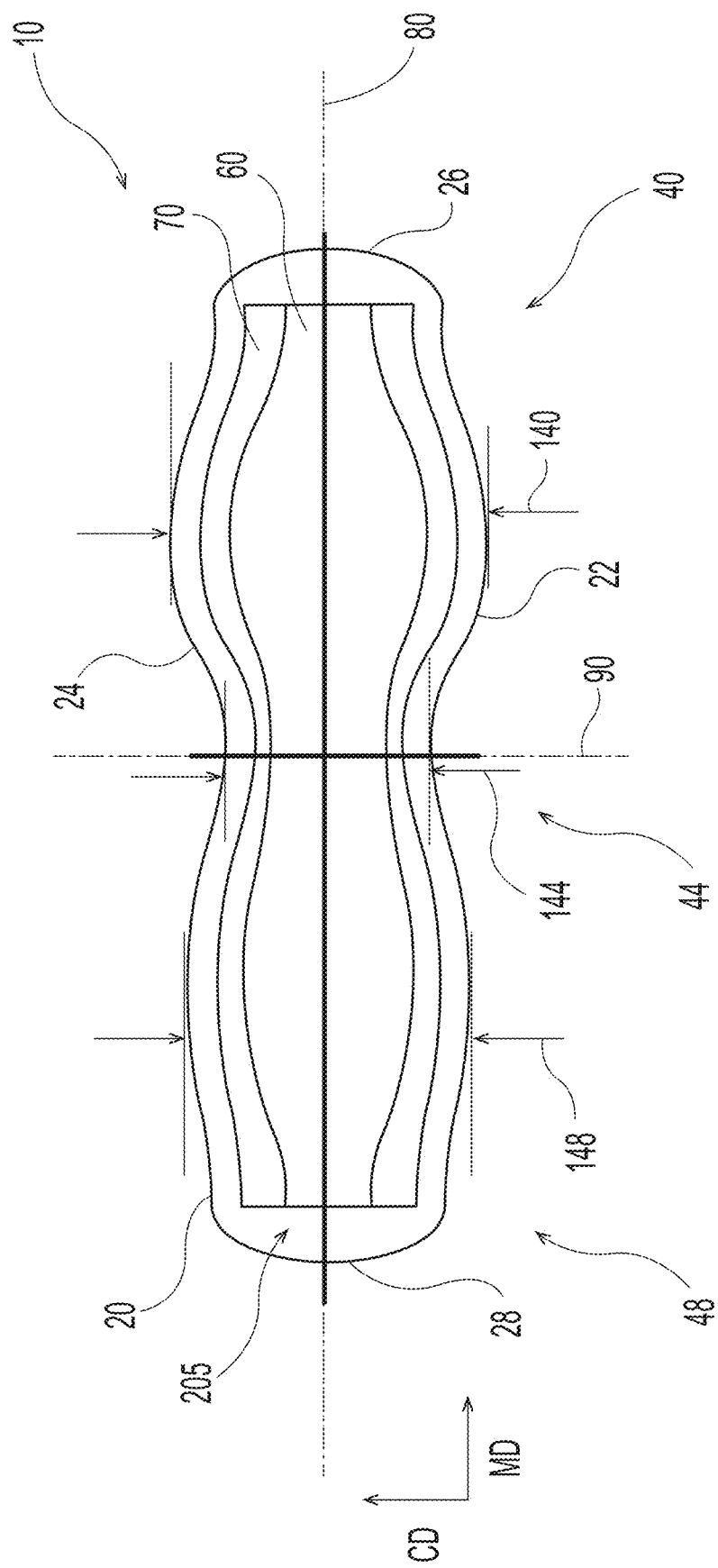
FIG. 1A is a representation of an absorbent article (excluding a topsheet and any optional intervening layers) constructed in accordance with the present disclosure.
Figure 1B:
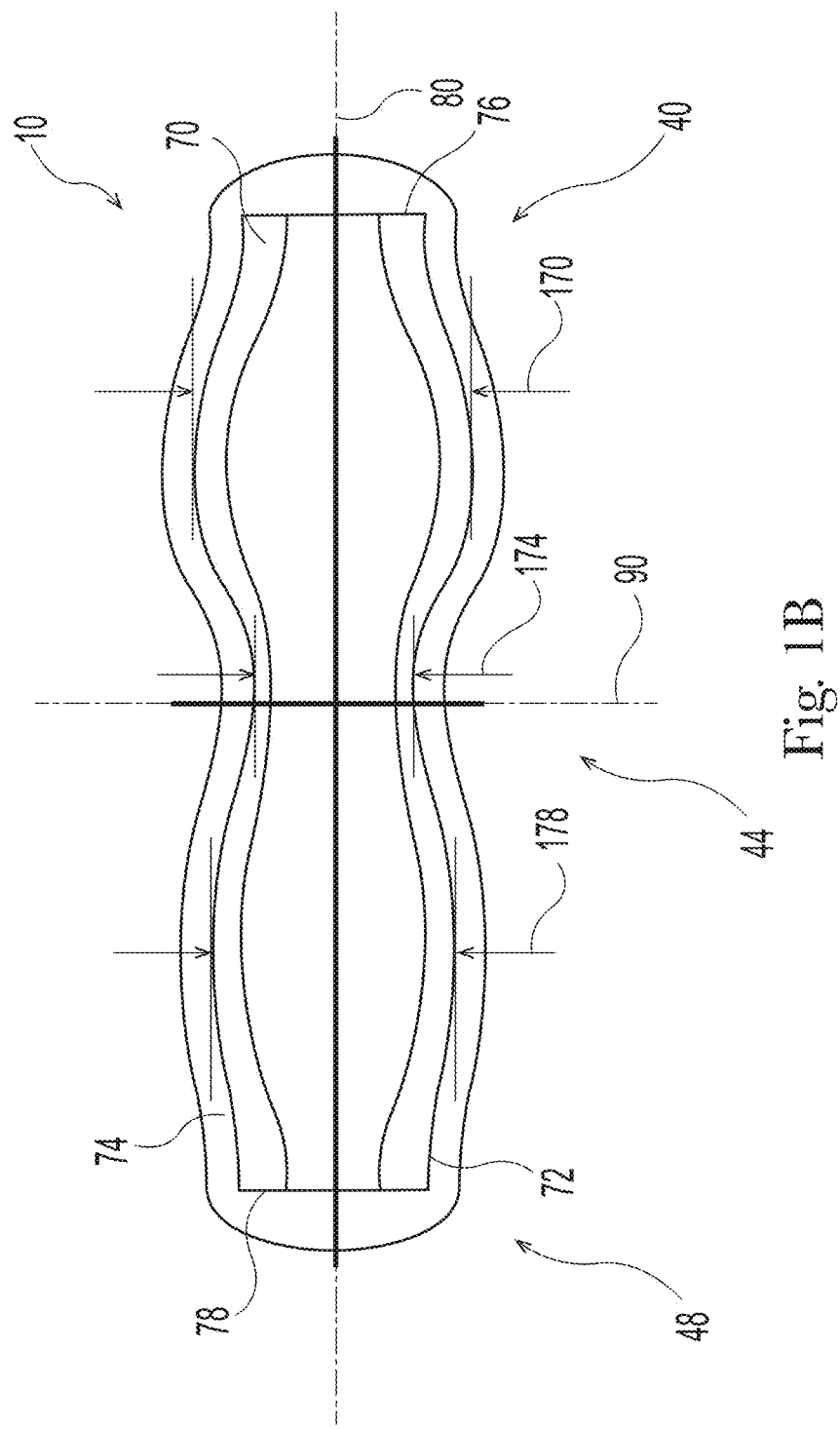
FIG. 1B is the representation of FIG. 1A showing various widths along the length of the article of a second absorbent core.
Figure 1C:
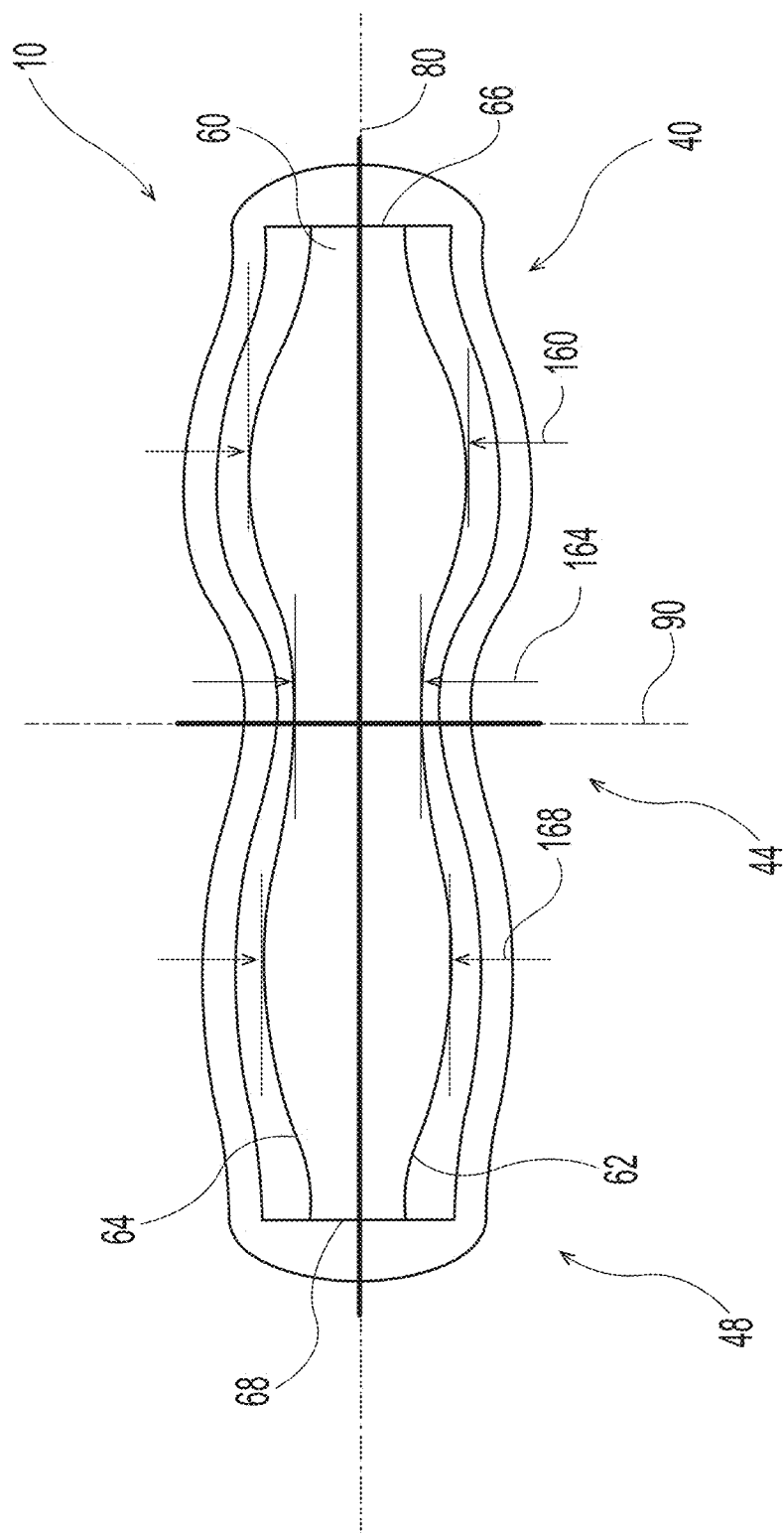
FIG. 1C is the representation of FIG. 1A showing various widths along the length of the article of a first absorbent core.

The following term explanations may be useful in understanding the present disclosure: "The disposable absorbent articles, particularly incontinence pads or pants, of the present invention can provide flexibility to allow for an improved and comfortable fit which is less susceptible to bunching during use. In particular, it is envisioned that the articles of the present disclosure exhibit heightened structural resiliency from the proposed configuration and orientation of the layers contained therein. For the purposes of this disclosure, reference to an incontinence pad, disposable absorbent article, or absorbent article will be used. However, the present invention may be applied to a plurality of absorbent articles including, but not limited to, sanitary napkins, pantiliners, menstrual pads, diapers, training pants, adult incontinence pants, etc.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The disposable absorbent articles, particularly incontinence pads or pants, of the present disclosure can provide flexibility to allow for an improved and comfortable fit which is less susceptible to bunching during use. In particular, it is envisioned that the articles of the present disclosure exhibit heightened structural resiliency from the proposed configuration and orientation of the layers contained therein while also allowing for conformance of the article.

There are several factors to consider when designing a disposable absorbent article like an incontinence pad, particularly if improved fit and performance are desired. First, the stiffness of the pad is an important factor. Typically, thinner pads offer less stiffness than their bulkier counterparts. Less stiffness can be desirable in some areas of the pad as the lower stiffness areas can allow the pad to conform as needed to the contours of a wearer; however, if not properly managed, then the absorbent article may offer no structural resistance to bunching/compression during wear which can lead to leakage. In contrast, while bulkier pads may be less likely to succumb to the compression that is typical during wear, bulkier pads are less desirable because they can cause the incontinence pad to lose its discreetness during use and become uncomfortable for the wearer. Additionally, despite resisting compressive forces during use, bulkier pads are not able to conform as easily as their thinner pad counterparts. This lack of conformance can similarly lead to leakage problems during use.

Second, is the absorbent capacity of the absorbent article. Ideally, the pad is well suited to accommodate either small or large loads of exudates. This accommodation means not only storing either type of load sufficiently but also effectively and quickly wicking such loads from a body-contacting surface of the pad such that the user experiences little to no feeling of wetness after the release of the load. In the case of a small load, a wearer should be able to continue to wear the pad for some reasonable time after a release since immediate changing of the pad may not be feasible or desired.

In the past, conventional incontinence pad designs have required a bit of compromise relative to these factors. In contrast, the absorbent articles designed pursuant to the present disclosure account for these factors to arrive at an absorbent article which exhibits improved protection against leakage, particularly for those wearers of a higher than average body mass index (BMI). Namely, absorbent articles of the present disclosure provide good core flexibility, excellent wicking, distribution, and overall absorbency, and in certain forms, may include barrier cuffs which stand up during use and contact the wearer in an appropriate location are included as part of the construction to further protect against a likelihood of leakage. For the purposes of this disclosure, reference to an incontinence pad, disposable absorbent article, or absorbent article will be used; however, the present disclosure may be applied to a plurality of absorbent articles including, but not limited to, sanitary napkins, pantiliners, menstrual pads, diapers, training pants, adult incontinence pants, etc.

FIG. 1A shows an absorbent article 10 according to the present disclosure. The absorbent article 10 may comprise a longitudinal centerline 80 and a lateral centerline 90. The longitudinal centerline 80 generally extends parallel to the longest dimension of the absorbent article 10. The lateral centerline 90 extends generally perpendicular to the longitudinal centerline 80 and lies in the same plane as the absorbent article 10 in a flattened state on a flat surface. The lateral centerline 90 bisects the length of the absorbent article 10 where the length is parallel to the longitudinal centerline 80, and the longitudinal centerline 80 bisects the width of the absorbent article 10 where the width is parallel to the lateral centerline 90. Additionally, as shown, the MD direction (machine direction) may be generally parallel to the longitudinal centerline 80 of the absorbent article 10, and the CD direction (cross-machine direction) may be generally parallel to the lateral centerline 90.

The absorbent article 10 further comprises a chassis 20 comprising an absorbent system 205 which, in some forms, comprises a first absorbent core 60 and a second absorbent core 70. As shown, the absorbent article 10 may comprise a generally hourglass shape. However, any suitable shape may be utilized. Some examples include offset hourglass (one end is wider than an opposite end and a narrowed midsection between the ends), bicycle seat shape (one end and central portion are narrower than second end), etc. Side edges 22 and 24 may follow the general contour of the first absorbent core 60 and/or the second absorbent core 70. So where, the first absorbent core 60 and/or the second absorbent core 70 are an hourglass shape, the side edges 22, 24 may be arranged in an hourglass shape as well. However, forms are contemplated where the side edges 22 and 24 are generally straight or slightly curved such that they do not follow the contour of the first absorbent core 60 and/or the second absorbent core 70. Additional details are discussed hereafter. The absorbent article 10 may be symmetric about the longitudinal centerline 80 or asymmetric about the longitudinal centerline 80. Similarly, the absorbent article 10 may be symmetric about the lateral centerline 90 or asymmetric about the lateral centerline 90.

As shown, the first absorbent core 60 may be positioned in absorbent article more proximal to a wearer-facing surface than the second absorbent core 70. However, forms are contemplated where the second absorbent core 70 is positioned in the absorbent article more proximal to a wearer-facing surface than the first absorbent core 60.

The plurality of side edges 22 and 24 extend generally parallel to the longitudinal centerline 80. A pair of end edges 26 and 28 join each of the side edges 22 and 24. One end edge 26 joins the side edges 22 and 24 in a first end region 40 of the absorbent article 10 while the other end edge 28 joins the side edges 22 and 24 in a second end region 48 of the absorbent article 10—the second end region 48 being opposite the first end region 40. An intermediate region 44 is disposed between the first end region 40 and the second end region 48.

The intermediate region 44 generally corresponds to the region of intended fluid entry for the article. For menstrual pads, the intended region of fluid entry may be the location on the menstrual pad that corresponds to the vaginal opening. For adult incontinence articles, the intended region of fluid entry may be the location of the incontinence article that corresponds to the urethra or the vulva region as labial tissue can obscure the pathway from the urethra to the absorbent article. And, in general, the intermediate region 44 may correspond to a portion of the absorbent article 10 that is positioned between the thighs of the wearer during use. In some forms, the intermediate region 44 may comprise the lateral centerline 90. In some forms, the intermediate region 44 may be asymmetrically disposed about the lateral centerline 90, e.g. disposed on one side of the lateral centerline 90 or disposed more on one side of the lateral centerline 90 than the other side of the lateral centerline 90. A method for determining the extent of the intermediate region 44 is described herein.

In one particular example, the intermediate region 44 extends a distance equal to 15% of the total length of the article from the expected insult point in a longitudinal direction. In some forms, the intermediate region 44 may comprise about 20 percent of the total length of the article, about 30 percent of the total length of the article, about 40 percent of the total length of the article or about 50 percent of the total length of the article, specifically including all values within these ranges and any ranges created thereby. The first end region 40 and/or the second end region 48 may comprise about 45 percent of the total length of the absorbent article, about 30 percent of the length of the absorbent article, about 20 percent of the length of the absorbent article, about 15 percent of the length of the absorbent article, any combinations thereof, specifically including all values within these ranges and any ranges created thereby.

The intermediate region 44 can be designed to accommodate varying BMI's of wearer's. For example, the intermediate region 44 may have an overall length of greater than about 25 mm, greater than about 30 mm, greater than about 40 mm, greater than about 50 mm, greater than about 60 mm, greater than about 70 mm, greater than about 80 mm, greater than about 90 mm, or greater than about 100 mm, specifically including all values within these ranges and any ranges created thereby. The longer lengths of intermediate region 44 can accommodate wearers with a larger BMI.

As shown, in some forms, the first end region 40 may have a first end region width 140 which represents the widest portion of the first end region. Similarly, the second end region 48 may comprise a second end region width 148 which represents the widest portion of the second end region 48. The intermediate region 44 may have an intermediate region width 144 which represents the narrowest portion of the intermediate region 44. In some forms, the first end region width 140 may be greater than the intermediate region width 144. In some forms, the second end region width 148 may be greater than the intermediate region width 144. In some forms, the first end region width 140 may be greater than the second end region width 148, or vice versa.

The lower width intermediate region 44 can accommodate various BMI's of wearers. For example, articles of the present disclosure may be positioned in a user's panty and are, at least in part, positioned between the thighs of the wearer. Regardless of the BMI of the wearer, the narrowest spacing to be realized by the absorbent article is generally between the thighs of the wearer. Conventional absorbent articles can tend to bunch in this area due to the narrow spacing. However, because of the narrower width of the intermediate region, absorbent articles of the present disclosure can more easily accommodate this spacing by aligning the intermediate region 44 with the space between the thighs of the wearer. Additionally, with an increase in BMI, the length of the narrow spacing between the thighs can increase. As such, in some forms, the length of the intermediate region 44 may be longer for higher BMI wearers than the length of the intermediate region 44 for lower BMI wearers.

As noted previously, forms are contemplated where the side edges 22 and 24 do not follow the contour of the first absorbent core 60 and/or the second absorbent core 70. In such forms, the intermediate region width 144 may be equal to the first end region width 140 and/or the second region width 148. However, in such forms, the first absorbent core 60 and/or the second absorbent core 70 may be contoured such that its respective width in the intermediate region 44 is narrower than at its respective first end width and/or second end width. Such forms can still accommodate the narrow spacing between the thighs of the wearer. For example, as noted previously, the absorbent core material of an absorbent article can often times be the stiffest portion of the absorbent article. As discussed hereafter, the absorbent system 205 of the absorbent article of the present disclosure are contoured. As such, it is believed that even where the side edges 22 and 24 are not contoured, the materials of the absorbent article 10 outside of the contoured absorbent system 205 can easily conform due to their lower stiffness.

Referring now to FIGS. 1A-IC, the first absorbent layer 60 may comprise side edges 62 and 64 and a pair of end edges 66 and 68 which join the side edges 62 and 64 in the first end region 40 and the second end region 48 of incontinence pad 10, respectively. Similarly, the second absorbent layer 70 may comprise side edges 72 and 74 and a pair of end edges 76 and 78 which join the side edges 72 and 74 in the first end region 40 and the second end region 48 of the incontinence pad 10, respectively.

Additionally, as shown the end edges 66 and 68 of the first absorbent layer 60 may be substantially flat. End edges 76 and 78 of the second absorbent layer 70 may be similarly configured. Moreover, in some forms, as shown, end edge 66 of the first absorbent layer 60 may be coterminous with end edge 76 of the second absorbent layer 70. In some forms, the first absorbent layer 60 and the second absorbent layer 70 may be positioned within the absorbent article 10 such that the first absorbent layer 60 is offset from the second absorbent layer 70. Such configuration is explained in additional detail hereafter.

As shown, the side edges 62 and 64 may be contoured such that an intermediate region first absorbent layer width 164 is less than a first region first absorbent layer width 160 and/or less than a second region first absorbent layer width 168. Similarly, the side edges 72 and 74 may be contoured such that an intermediate region second absorbent layer width 174 is less than a first region second absorbent layer width 170 and/or less than a second region second absorbent layer width 178.

In some forms, the first region first absorbent layer width 160 may be less than the first region second absorbent layer width 170. In some forms, the second region first absorbent layer width 168 may be less than the second region second absorbent layer width 178. In some forms, the intermediate region first absorbent layer width 164 may be less than the intermediate region second absorbent layer width 174. In some forms, one or more of the foregoing widths for the first absorbent core 60 may be the same as, greater than, less than, or any combination thereof, of one or more of the foregoing widths for the second absorbent core 70.

In addition to the contouring of the absorbent system 205 mentioned above, it is believed that the smaller width of the first absorbent core 60 also facilitates conformance of the absorbent article. As mentioned previously, the stiffest materials of the absorbent article 10 are in the absorbent system 205. So for those areas where the first absorbent core 60 and the second absorbent core 70 overlap one another, a higher level of stiffness is present as opposed to those areas where the second absorbent core 70 extends outboard of the first absorbent core 60. For those areas of the absorbent article where the second absorbent core 70 extends outboard of the first absorbent core 60, stiffness is much less than for those areas where the first absorbent core 60 and the second absorbent core 70 overlap.

In some forms, the amount of the second absorbent core 70 outboard of the first absorbent core 60 can be constant along the length of the first absorbent core 60. In such forms, it is believed that a minimum portion of the second absorbent core 70 outboard of the first absorbent core 60 is greater than 5 mm. It is believed that this minimum distance can be beneficial in allowing sufficient conformance of the absorbent article. However, forms are contemplated where the portion of the second absorbent core 70 outboard of the first absorbent core 60 may be variable depending on location. Examples regarding this aspect of the absorbent article of the present disclosure are provided hereafter.

Figure 1D:
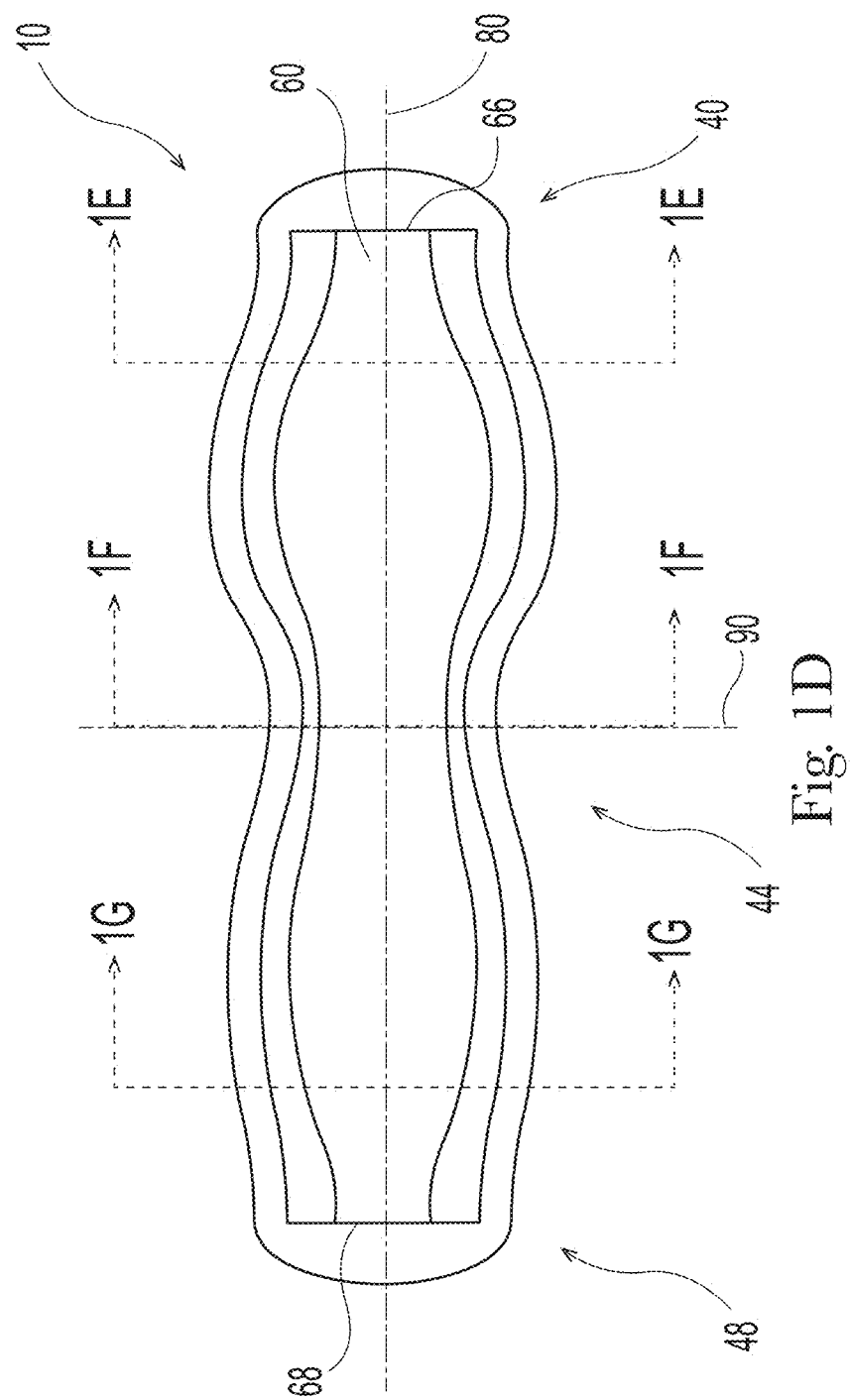
FIG. 1D is the representation of FIG. 1A highlighting various cross sections along the length of the article.
Figure 1E:
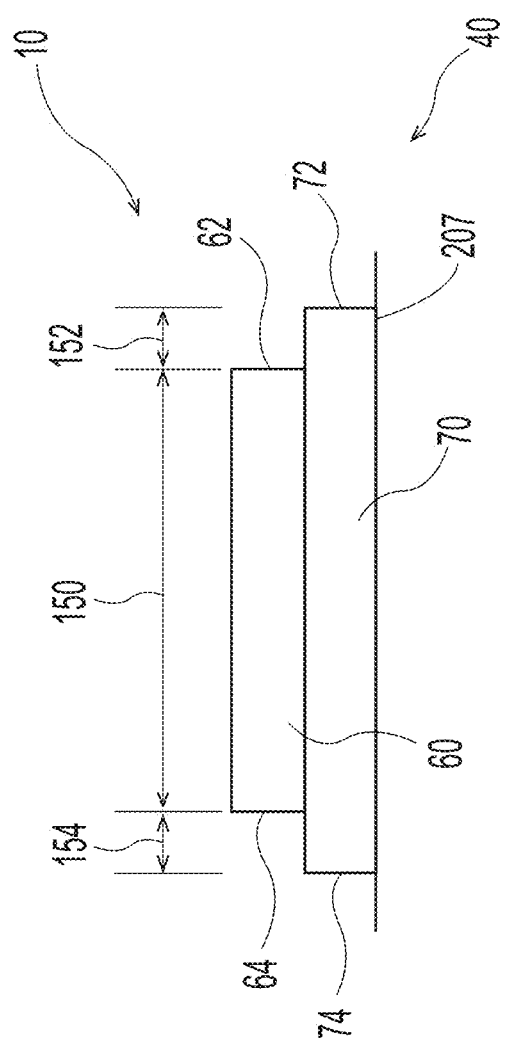
FIG. 1E is a representation of a cross section of the article of FIG. 1A in a first end region along line 1E-1E.

Referring now to FIGS. 1D-1E, a cross sectional view of the absorbent article 10 in the first end region 40 is shown. As described previously, the first absorbent core side edges 62 and 64 may be laterally inboard of the second absorbent core side edges 72 and 74. The distance between the side edge 62 and side edge 72 is a first outboard distance 152, and the distance between the side edge 64 and 74 is a second outboard distance 154. And the region between the first outboard distance 152 and the second outboard distance 154 is an overlap distance 150. As described above, it is believed that sufficient conformity can be derived where the first outboard distance 152 and the second outboard distance 154 are greater than 5 mm, particularly in the intermediate region 44. However, where the first end region 40 corresponds to the front of the article, the first end region 40 is generally positioned anteriorly of the vaginal opening as well as anteriorly of the urethral opening. In this area of the body, the body contour is typically flat across a wide range of wearer BMI's. Due to the flatter body surface, conformance by the absorbent article in the first end region 40 may not be as critical as in other areas. So, the first outboard distance 152 and the second outboard distance 154 in the first end region 40 may be less than 10 mm. In some forms, the outboard distance 152 and 154 may between 0 mm and 7 mm, between 1 mm and 5 mm, and between 2 mm and 4 mm, specifically including all values within these ranges and any ranges created thereby. In some forms, the first outboard distance 152 and/or second outboard distance 154 may be 0 mm.

The overlap distance 150 can be any desired value that is comfortable to a wearer and can accommodate expected loading by the wearer. In some forms, the overlap distance 150 may be between about 10 mm to about 30 mm, from about 20 mm to about 40 mm, from about 25 mm to about 50 mm, or greater than about 60 mm, specifically including all values within these ranges and any ranges created thereby.

The outboard distances 152 and 154 may gradually increase from the first end region 40 toward the intermediate region 44. As noted previously, the intermediate region 44 is generally a portion of the absorbent article 10 that is positioned between the thighs of a wearer during use. Due to the limited spacing between the thighs of the wearer, excess material of the absorbent article may tend to compress/bunch if not carefully controlled. Such compression/bunching can increase the likelihood of leakage. As such, in the intermediate region 44, conformance of the absorbent article 10 is paramount to reducing the likelihood of leakage.

Referring now to FIGS. 1D and 1F, in the intermediate region 44, the outboard distances 152 and 154 may be greater than 5 mm. In some forms, the outboard distances 152 and/or 154 can be greater than 5 mm, at least 7 mm, at least 8 mm, at least 10 mm, at least 15 mm, or at least 20 mm, specifically including all values within these ranges and any ranges created thereby. In the intermediate region 44, the outboard distances may be between about 5 mm to about 20 mm, from about 7 mm to about 18 mm, or from about 8 mm to about 15 mm. However, where outboard distances 152 and/or 154 are higher than 20 mm, the absorbent article 10 may be too conforming. Unfortunately, where the absorbent article is too conforming, this can cause the absorbent article 10 to compress/bunch thereby increasing the likelihood of leakage. In contrast, wherein the outboard distances 152 and 154 are less than or equal to 5 mm, increased forces may be required to drive conformance of the absorbent article 10. Such increased forces may cause discomfort to the wearer during use.

Additionally, the overlap distance 150—in the intermediate region 44—may be at least 10 mm, at least 20 mm, or at least 30 mm, specifically including all values within these ranges and any ranges created thereby. For higher BMI wearers e.g. 30 or greater, the overlap distance 150 may be less than 50 mm, less than 40 mm, less than 30 mm, or about 20 mm, specifically including all values within these ranges and any ranges created thereby. For those wearers with a lower BMI, e.g. 30 or less, the overlap distance 150 may be greater than about 20 mm, greater than about 30 mm, greater than about 40 mm, greater than about 50 mm, greater than about 60 mm, specifically including all values within these ranges and any ranges created thereby.

Additionally, forms are contemplated where the outboard distances 152 and 154 in the intermediate region 44 are achieved via the first absorbent core 60 being outboard of the second absorbent core 70. Such configurations may be beneficial for higher BMI wearers, e.g. 30 or greater. For these higher BMI wearers, the space (width) available adjacent the vaginal opening or urethral opening may be greater than the space (width) available between the thighs. So, a wider first absorbent core 60 which is more proximal to the wearer than the second absorbent core 70 can be beneficial.

With the above in mind, arrays of products may be created which can accommodate a wide variety of BMI's. For example, for lower BMI's, the outboard distances and overlap distances can be configured in a first plurality of products for lower BMI wearers and configured in a second plurality of products for higher BMI wearer.

Referring now to FIGS. 1D and 1G, much like the first end region 40, the outboard distances 152 and 154 in the second end region 48 can be any suitable value. In general, the second end region 48 of the absorbent article 10 is disposed posteriorly of the vaginal opening and is typically positioned adjacent the gluteal sulcus (the gluteal sulcus is often referred to as the fold of the buttock or the gluteal fold of the horizontal gluteal crease). Similar to the first end region 40, the second end region 48 of the absorbent article 10 generally does not experience bunching/compression to the same extent as the intermediate region 44. Additionally, for those forms of the absorbent article 10 which comprise menstrual pads or adult incontinence pads, the areas of fluid insult generally correspond to the intermediate region 44 and/or the first end region 40. So, for such absorbent article forms absorbent capacity in the second end region 48 may not be as critical as it is for the first end region 40 and/or the intermediate region 44. Accordingly, the outboard distances 152 and 154 in the second end region 48 can be any suitable value. Similarly, the overlap distance 150 can be any suitable value. It is worth noting that absorbent capacity in the second end region 48 can provide the wearer with some sense of confidence. So, even if mainly cosmetic, absorbent capacity in the second end region 48 may be a good choice-particularly where the second end region 48 is adjacent to the intermediate region 44.

Figure 1H:
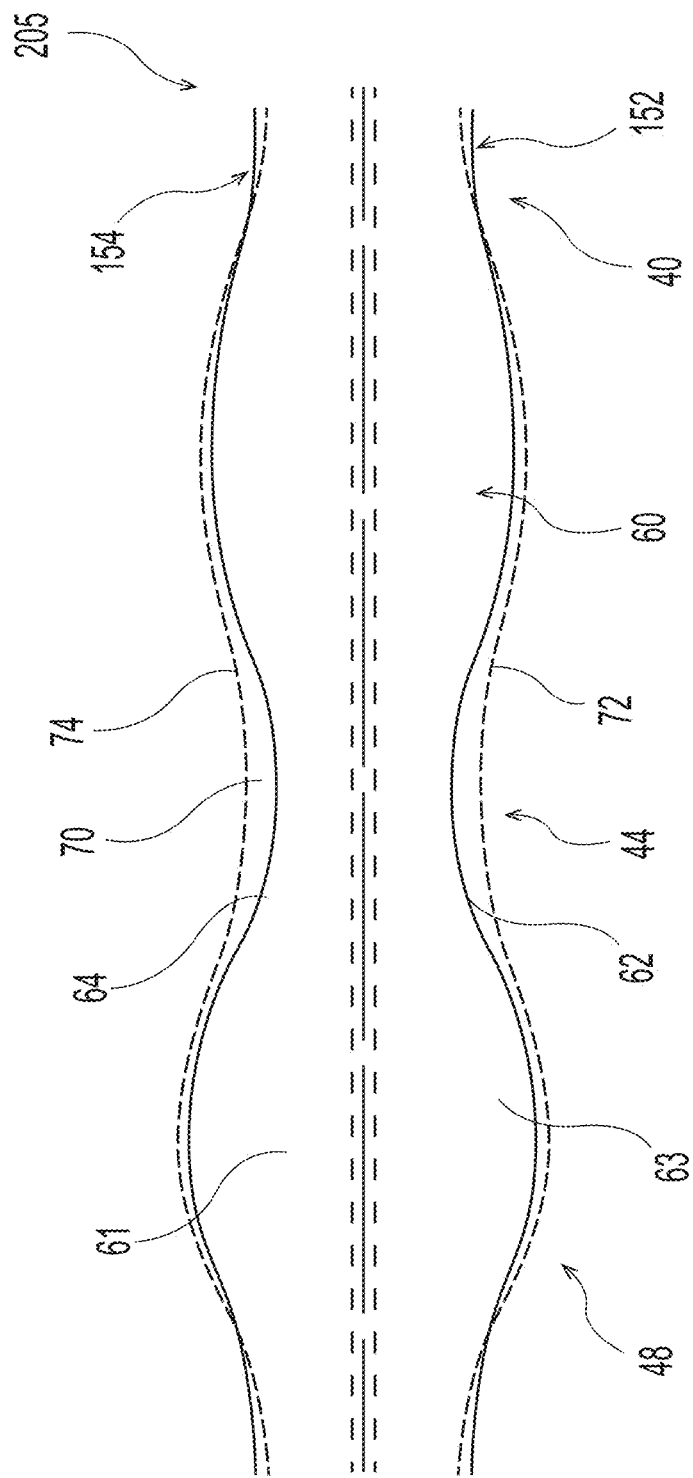
FIG. 1H shows an alternative configuration of an absorbent system which can be utilized in the absorbent articles of the present disclosure.

Referring now to FIGS. 1H and 1I, examples of variable outboard distances 152 and 154 are shown. Additionally, outboard edges of the absorbent cores 60 and 70 are shown as variable. Regarding FIG. 1H, forms are contemplated where the edges 62 and 64 of the first absorbent core 60 are disposed outboard of the edges 72 and 74 of the second absorbent core 70 in the first end region 40, the second end region 48, and/or the intermediate region 44. Regarding FIG. 1I, in some forms, the outboard distance 152 and 154 may be variable within a particular region of the article. For example, the outboard distance 152 and 154 may be variable within the intermediate region 44. In some forms, at least a portion of the outboard distances 152 and/or 154 in the intermediate region 44 may be equal to or less than the 5 mm described heretofore. In such forms, it may be beneficial to configure the lower outboard distances 152 and 154, i.e. equal to or less than 5 mm toward the ends of the intermediate region 44. So for such forms, the lower outboard distances would be disposed adjacent the first end region 40 and the second end region 48.

Figure 2A:
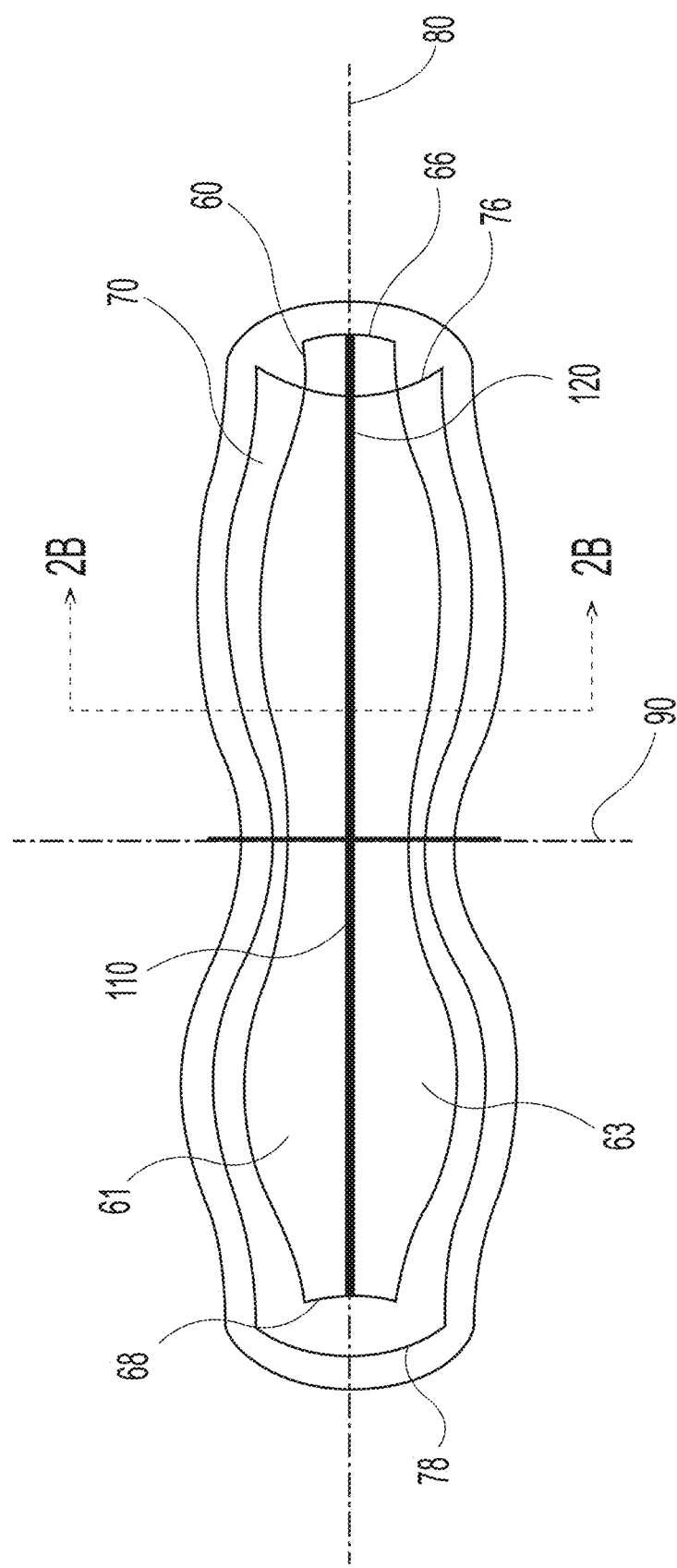
FIG. 2A is a representation of another configuration of an absorbent article (excluding the topsheet and any optional intervening layers) constructed in accordance with the present disclosure.

Referring now to FIG. 2A, in some forms, the end edges 66 and/or 68 of the first absorbent layer 60 may be contoured. For example, end edge 66 of the first absorbent core 60 may have a convex (male) configuration while end edge 68 may have a concave (female) configuration. In contrast, end edge 76 of the second absorbent core 70 may have a concave (female) configuration while the end edge 78 of the second absorbent core 70 has a convex (male) configuration. The convex/concave configurations of the first absorbent core 60 and/or the second absorbent core 70 can minimize the amount of scrap generated during manufacturing of the absorbent articles of the present disclosure. Additional arrangements of the absorbent core layers and processing of the absorbent article of the present disclosure are described in additional detail hereafter.

Figure 2B:
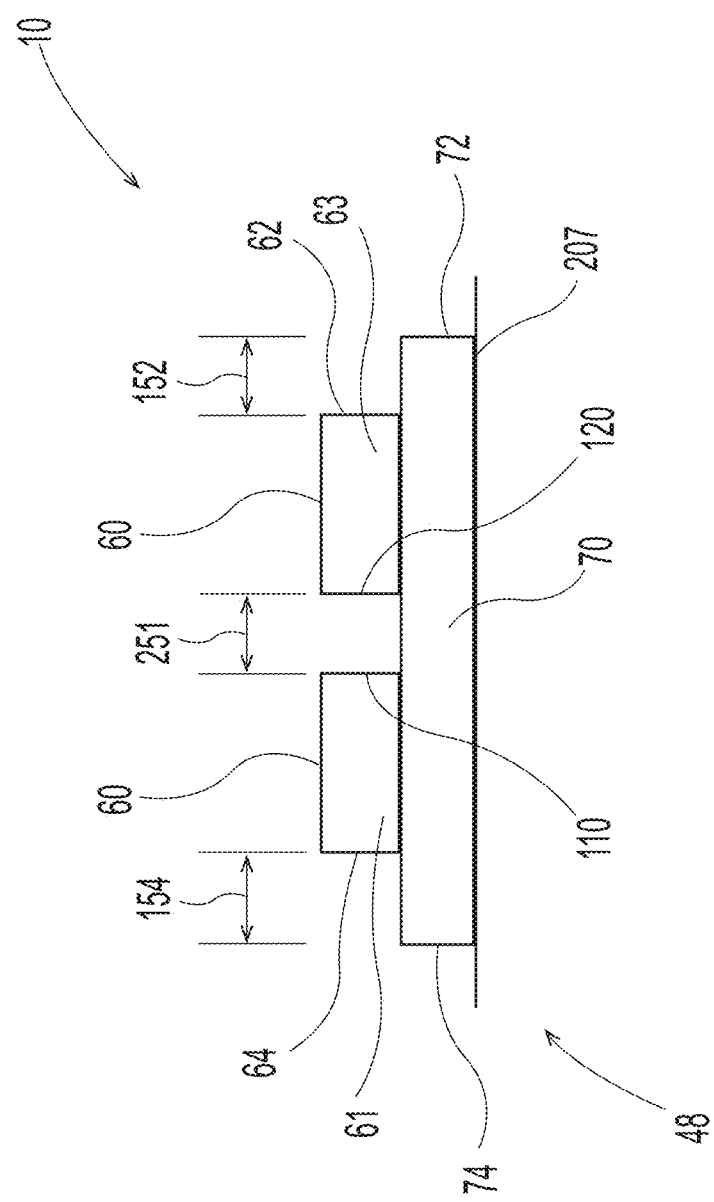
FIG. 2B is a representation of a cross section of the article of FIG. 2A along line 2A-2A.

Referring now to FIGS. 2A and 2B, in some forms, the first absorbent core 60 may comprise a first portion 61 and a second portion 63. The first portion 61 and the second portion 63 may be discrete portions of the first absorbent core 60. For example, a separation 251 between the first portion 61 and the second portion 63 may coincide with the longitudinal centerline 80. In some forms, the separation 251 between the first portion 61 and the second portion 63 may, at least in part, be offset from the longitudinal centerline 80. The first portion 61 may comprise a first finished edge 110, and the second portion 63 may comprise a second finished edge 120. In some forms, the first finished edge 110 and the second finished edge 120 may abut one another such that separation 251 between the first finished edge 110 and the second finished edge 120 is minimal. In other forms, the separation 251 may be more substantial. For example, in some forms the separation 251 can be greater than about 0.5 mm, greater than about 1.0 mm, greater than about 1.5 mm, greater than about 2.0 mm, greater than about 3.0 mm, greater than about 4.0 mm, up to about 5.0 mm, specifically including all values within these ranges and any ranges created thereby.

It is worth noting that the separation 251 between the first portion 61 and the second portion 63 can facilitate folding of the absorbent article 10 in the area of the separation 251. As discussed previously, due to the decreased stiffness of the absorbent article 10 in the area of the separation 251, folding of the article in this area may be facilitated during use. However, if the gap is too large, then the absorbent article 10 can be much more susceptible to bunching which can increase the likelihood of leakage. To reduce the likelihood of leakage, the separation 251 is preferably less than or equal to 2 times the caliper of the first portion 61 and/or second portion 63. In some forms, the separation 251 may be less than or equal to 1.5 times the caliper of the first portion 61 and/or second portion 63. In some forms, the separation 251 can be less than or equal to about 1 times the caliper of the first portion 61 and/or second portion 63.

The outboard distances 152 and 154 discussed herein are equally applicable to the forms shown in FIGS. 2A-2B. Similarly, the overlap distance 150 (shown in FIGS. 1E-1G) can be equally applicable for the forms in FIGS. 2A-2B.

Figure 3:
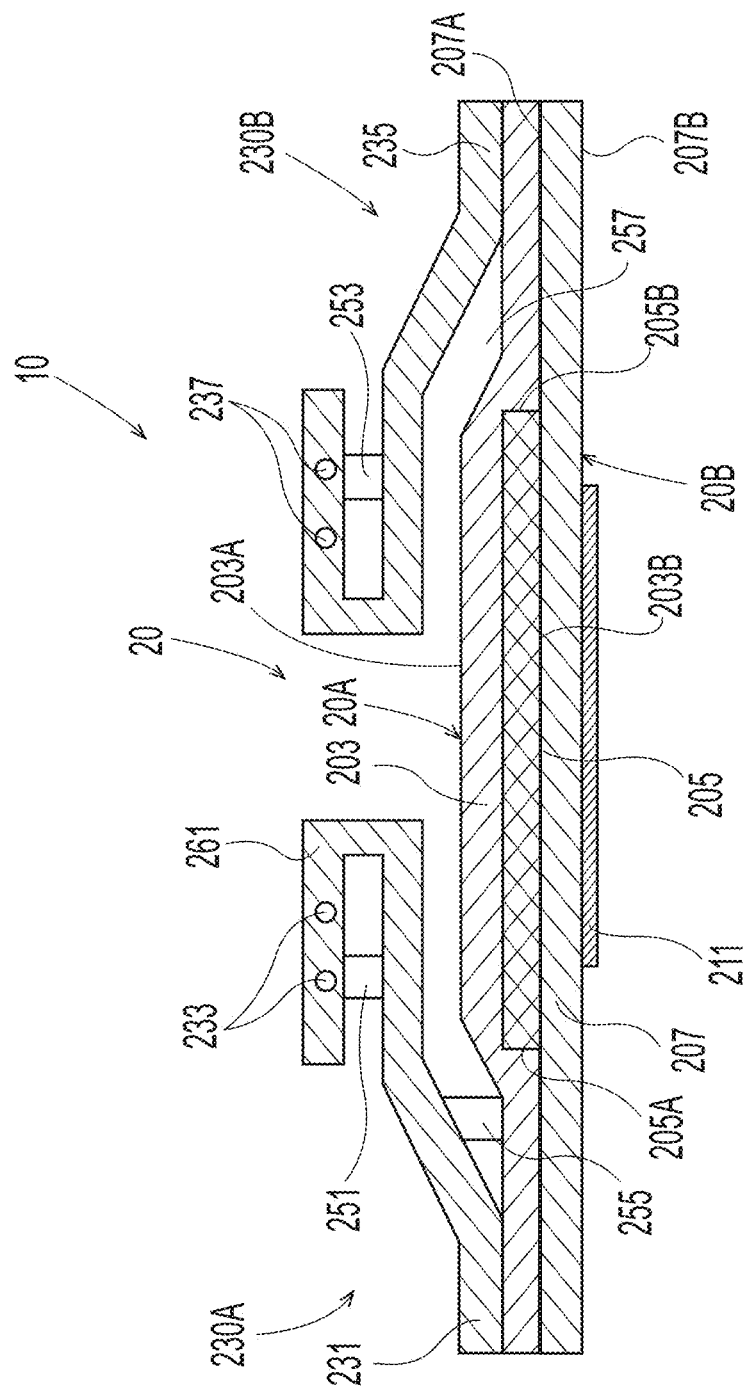
FIG. 3 is a representation of a cross section of an article constructed in accordance with the present disclosure.

Referring now to FIGS. 1A-3, the chassis 20 of an exemplary absorbent article is shown in cross-section in FIG. 3, the cross section being taken along the lateral centerline 90. Among other things, the chassis 20 comprises a primary topsheet 203. This primary topsheet has a body-facing surface 203A and a garment-facing surface 203B. This chassis 20 of the pad 10 further comprises a backsheet 207 which also comprises its own body-facing surface 207A and opposing garment-facing surface 207B. These two components sandwich the absorbent system 205. In other words, the absorbent system 205 is disposed between the topsheet 203 and the backsheet 207. All three components (i.e., topsheet 203, backsheet 207, and absorbent system 205) form the chassis 20 of the pad 10. Additional layers may very well be included within this chassis 20, particularly between the topsheet 203 and the backsheet 207 but it should be noted that these layers are separate and apart from the absorbent system. Suitable additional layers may include secondary topsheets, acquisition layers, additional distribution layers over and above those which will be discussed below, and other useful layers. In the case of a secondary topsheet, it is disposed beneath the primary topsheet 203 and on the body-facing surface of the core. In some forms, the secondary topsheet (also known as the "STS") has a greater length and width than the absorbent system 205. In some forms, the chassis may further comprise barrier cuffs 230A and 230B. The barrier cuffs are discussed in additional detail hereafter.

The chassis 20 further comprises a wearer-facing surface 20A and a garment-facing surface 20B. The wearer-facing surface 20A may comprise the topsheet 203, and the garment-facing surface 20B may comprise the backsheet 207.

Figure 4:
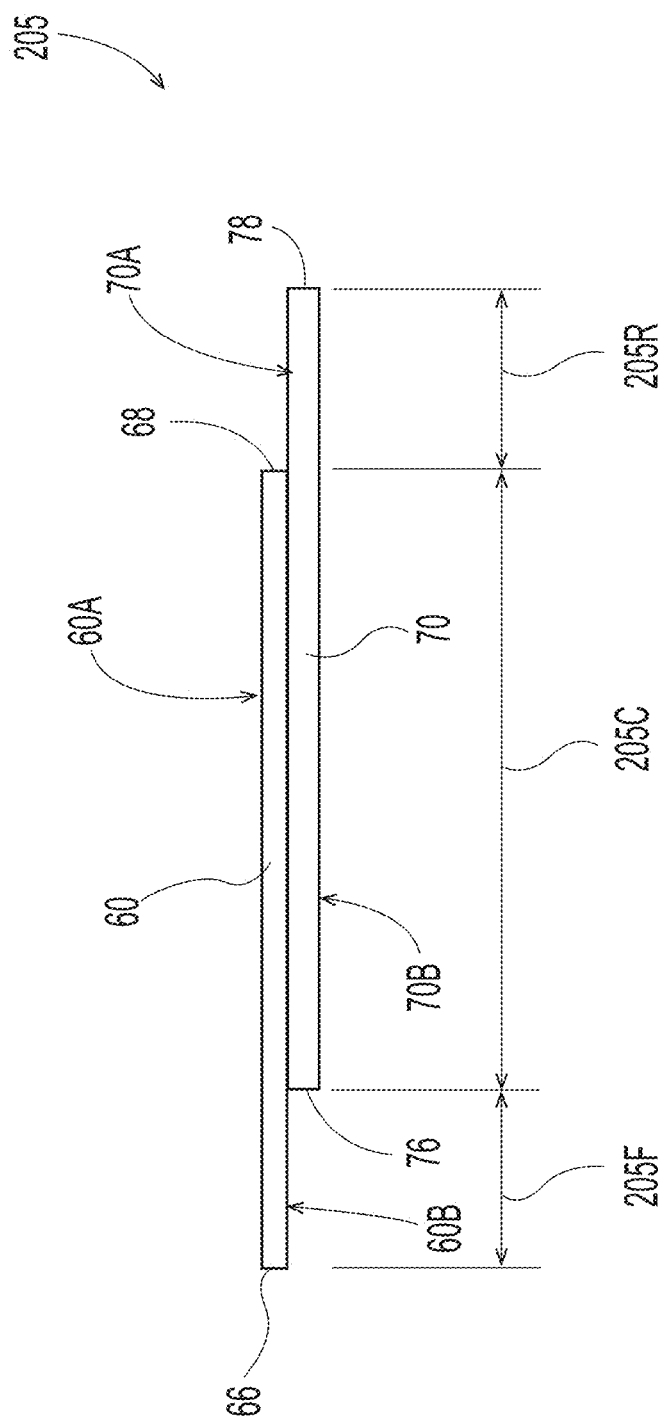
FIG. 4 is a representation of an absorbent system which is suitable for use with absorbent articles of the present disclosure.

Referring now to FIG. 4, a cross section of an exemplary absorbent system 205 taken along a longitudinal centerline is shown. As noted previously, the absorbent system 205 may comprise a first absorbent core and a second absorbent core 70. As shown, the first absorbent core 60 has an upper surface 60A and a lower surface 60B which opposes the upper surface. Similarly, the second absorbent core 70 has an upper surface 70A and a lower surface 70B. Additionally, in some forms, the first absorbent core 60 and/or the second absorbent core 70 may comprise a laminate structure which includes a plurality of layers. Such forms are discussed in additional detail hereafter.

As shown, in some forms, the first absorbent core 60 may be joined to the second absorbent core 70 in an offset manner or configuration along the length of the absorbent system 205. As used herein "offset" or "offset manner" means that the layers of interest are staggered and that their respective end edges are not aligned in a z-direction (i.e., the end edge of one layer or laminate structure is not coterminous with the end edge of an adjacent underlying or overlying layer or laminate structure) when the layers or laminate structures overlay one another. This offset joinder of the first and second absorbent cores 60 and 70 results in an overlapping and joined area of the two layers that forms a central portion 205C of the absorbent system 205. The central portion 205C of the absorbent system 205 is consequently bounded on each side by a front end portion 205F and a rear end portion 205R, both of the absorbent system 205. In other words, the front end portion 205F and the rear end 205R portion are respectively disposed at opposing ends of the absorbent system 205. As shown in some forms, a distance between the end edge 66 and the end edge 76 can define a length of the front end portion 205F. Similarly a distance between the end edge 78 and the end edge 68 can define a length of the rear end portion 205R. In some forms, the end edge 76 may be the leading edge (more proximal to the first region 40 of the pad 10) of the absorbent system 205 while the end edge 68 may be the trailing edge (more proximal to the second region 48 of the pad 10) of the absorbent system 205.

The length of the central portion 205C can vary by size of the absorbent article 10. For example, for those absorbent articles sized for higher BMI wearers, the length of the central portion 205C can be higher than the central portion 205C for absorbent articles sized for wearers having a lower BMI. Additionally, where the absorbent articles are equipped with elasticated barrier leg cuffs, the central portion 205C may extend past the outermost anchor points of the elastomeric members of the barrier leg cuffs. Extension of the central portion 205C past these outermost anchor points can reduce the likelihood of the ends of the absorbent article folding during application of the absorbent article. Folding ends during application of the absorbent article can be problematic as described in U.S. Patent Application No. 2017/0049634. In some forms, the central portion 205C may have a length of at least 50 mm, at least 75 mm, at least 90 mm, at least 100 mm, at least 125 mm, at least 150 mm, at least 175 mm, at least 200 mm, at least 225 mm, at least 250 mm, 275 mm, 300 mm, 325 mm, 350 mm, or 375 mm, specifically including all values within these ranges and any ranges created thereby.

Processing of such forms can be facilitated according to the process of the present disclosure. As shown in FIGS. 2-6, an absorbent core web 500 can be obtained from a supplier or can be manufactured by an absorbent article manufacturer. Additional details of the absorbent core web 500 will be provided in additional detail hereafter. As shown, the absorbent core web 500 can be transported in a machine direction to a slitting machine 510. Slitting machines are well known in the art.

In some forms, and absorbent core web 500 can be slit along slit lines 562 and 564 which can be offset from a longitudinal centerline 580 of the absorbent core web 500. As shown, post slitting, three separate webs may be created, namely, a first absorbent core first portion web 561, a first absorbent core second portion web 563, and a second absorbent core web 570. The slitting of the absorbent core web 500 can reduce the production of scrap material generated via processing of the web. For example, finished edges of the web 510 and 520 can be utilized in the first portion 61 and second portion 63 of the first absorbent core 60 as the first finished edge 110 and the second finished edge 120, respectively. Additionally, the edges of the first portion web 561 created by slit line 562 may be utilized in the first portion 61 of the first absorbent core 60 as side edge 62 and as side edges 72 for the second absorbent core 70. Similarly, the edges created by the slit line 564 may be utilized by the second portion 63 of the first absorbent 60 as the side edge 64 and as the side edge 74 for the second absorbent core 70.

In some forms, the first absorbent core first portion web 561 and the first absorbent core second portion web 563 may then be provided to a cutting device 520A to cut discrete first portions 561A and discrete second portions 563A from theses absorbent core webs, respectively. Similarly, the second absorbent core web 570 may be provided to a cutting device 520B to cut discrete second absorbent core layers 570A from the second absorbent core web 570. Exemplary cutting devices are known in the art. And, cutting devices for the creation of convex/concave end edges are disclosed in U.S. Patent Application Publication No. 2018/0154533.

In some forms, the cutting of the first absorbent core first portion web 561 and the first absorbent core second portion web 563 may be facilitated via the introduction of a first carrier web upstream of the cutting device 520A. In such forms, the first absorbent core first portion web 561 and the first absorbent core second portion web 563 can be combined with the first carrier web. The first absorbent core first portion web 561 and the first absorbent core second portion web 563 can be positioned on the first carrier web in their appropriate orientation, e.g. separation 251 between the first portion and second portion is provided as described herein. The first absorbent core portions and carrier web can then be provided to the cutting device simultaneously. From the cutting device a plurality of discrete first absorbent cores may be provided.

Still referring to FIGS. 2-6, as shown, the cutting device 520A can provide the first absorbent core 60 (both the first portion and second portion) with a convex (male) end edge 66 while the second cutting device 520B can provide the second absorbent core layer 70 with a concave (female) end edge 76. However, forms are contemplated where both the end edges 66 and 76 are convex (male). Forms are contemplated where both the end edges 66 and 76 are concave (female). Forms are contemplated where the end edge 66 is concave (female) and the end edge 76 is convex (male). Additional forms are contemplated where at least one of the end edges of the first absorbent core 60 (the first portion and/or the second portion) and/or the second absorbent core layer 70 are neither convex nor concave, e.g. substantially flat, wavy, etc. The end edges of the first and second ends of each of the first and second absorbent cores may have shapes selected from the group consisting of arcs, semicircles, semi-ellipses, chevrons, rectangles, sinusoids, jigsaws, and combinations thereof.

From the cutting device 520A, the plurality of discrete first absorbent core first portions 561A is provided to a cut-and-slip or cut-and-lay operation 530A. Similarly, the first absorbent core second portions 563A may be provided to the same cut-and-slip or cut-and-lay operation 530A as the first absorbent core first portion layers 561A. Or in some forms, the first absorbent core second portion layers 563A may be provided to a separate cut-and-slip or cut-and-lay operation. As noted above, where the first absorbent core first portion web 561 and the first absorbent core second portion web 563 are provided to the first carrier web, the plurality of discrete first absorbent cores can then be provided to a single cut-and-slip or cut-and-lay operation.

The cut-and-slip or cut-and-lay operation 530A can position one of the plurality of first absorbent core first portions 561A and/or first absorbent core second portions 563A onto a carrier web. For those forms where the first carrier web is introduced prior to the cutting device 520A, the discrete first absorbent core portions may be placed onto a second carrier web via the cut-and-slip or cut-and-lay operation 530A. Regardless of when the carrier web is introduced into the process, the first absorbent core first portions 561A and the first absorbent core second portions 563A placed onto the first and/or second carrier web, may be oriented such that the convex (male) end edge is the leading edge in the machine direction or the concave (female) end edge is the leading edge. The placement of the first absorbent core first portions 561A and first absorbent core second portions 563A onto the carrier web post the cut-and-slip or cut-and-lay operation 530A forms an absorbent core pre-cursor web 580.

Similarly, from the cutting device 520B, the plurality of discrete second absorbent cores 570A is provided to a cut-and-slip or cut-and-lay operation 530B. The cut-and-slip or cut-and-lay operation 530B can position one of the plurality of discrete second absorbent cores 570A onto the absorbent core pre-cursor web 580. In such forms, the second absorbent core layer 70 may be provided in an offset manner such that its upper surface 70A is attached to the lower surface 60B of the first absorbent core layer 60. The second absorbent core layer 70 and the first absorbent core layer 60 may be attached in any suitable manner, e.g. adhesives.

Figure 5:
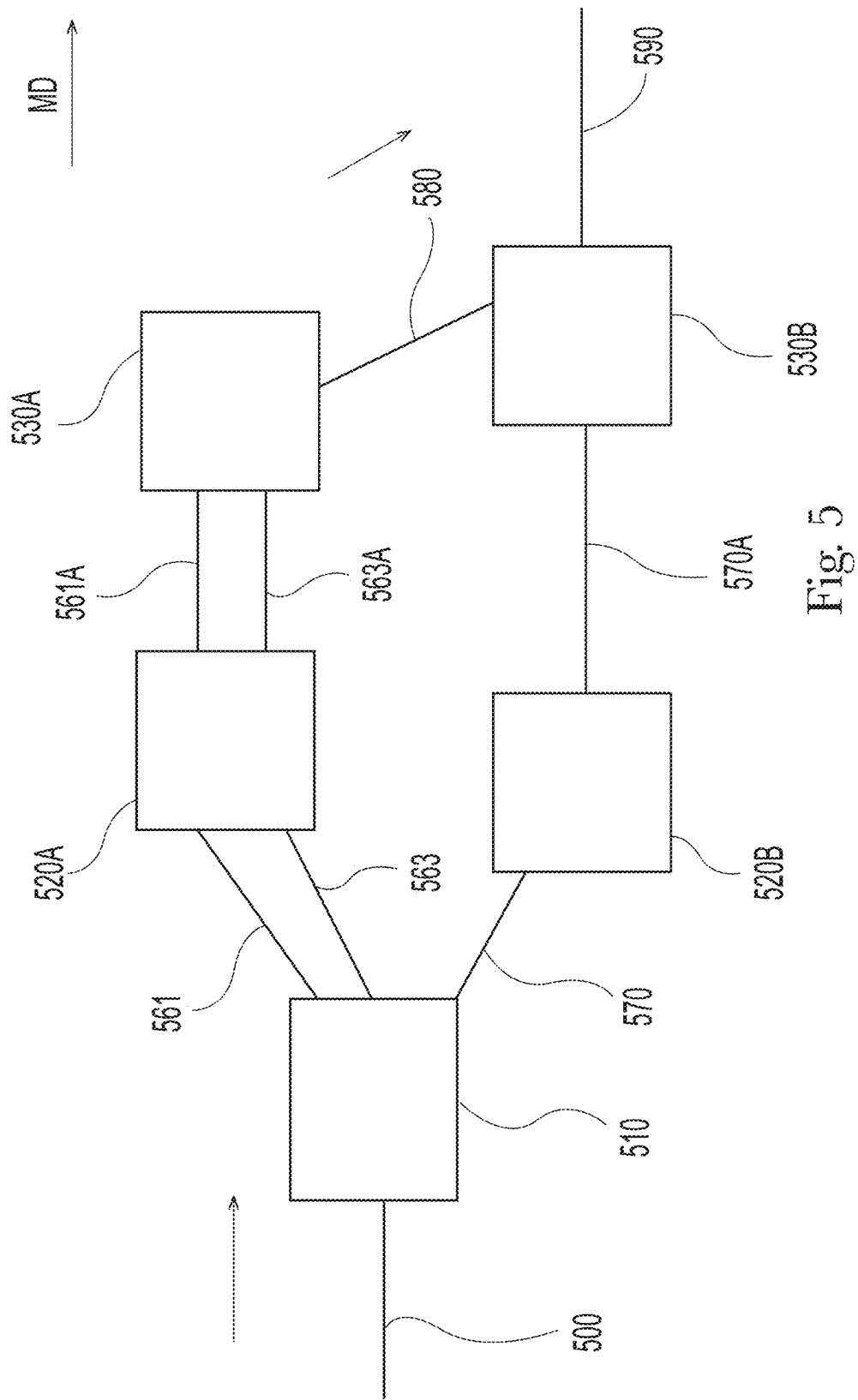
FIG. 5 is a schematic representation of a process which can be utilized for making absorbent systems in accordance with the present disclosure.
Figure 6:
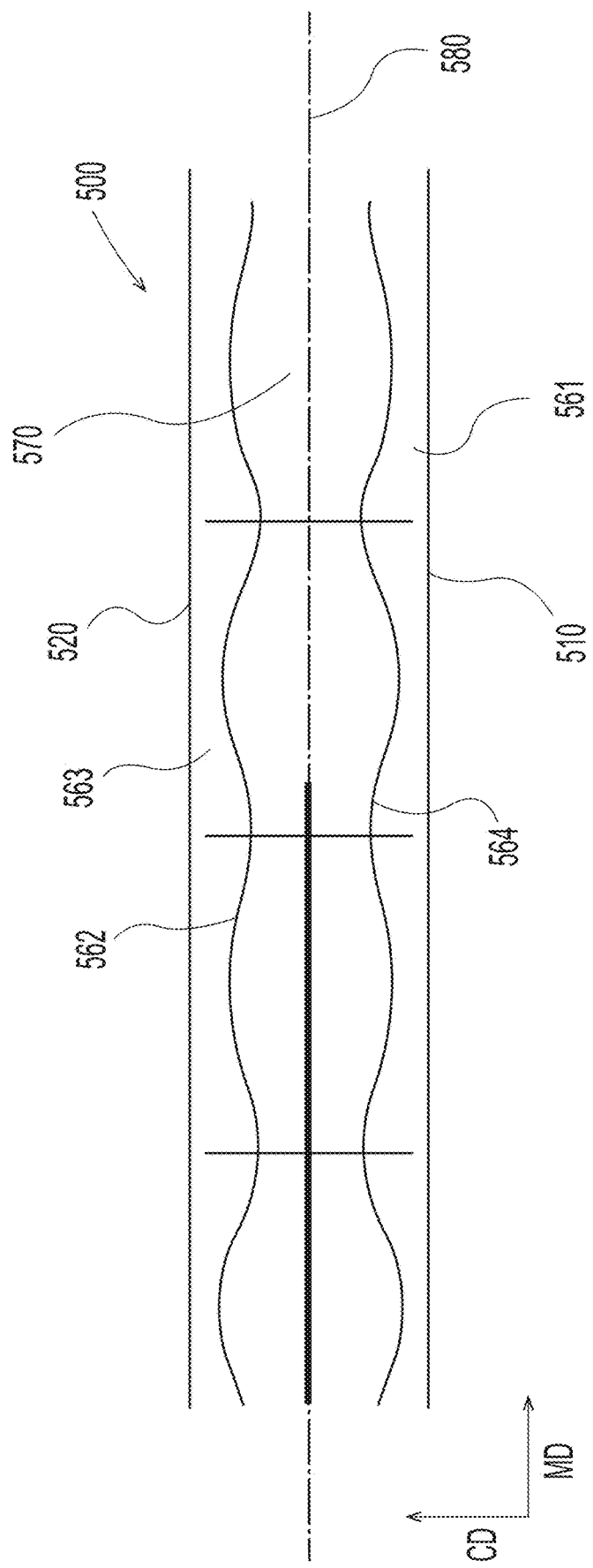
FIG. 6 is a representation of an absorbent core web showing various slit lines.

It is worth noting that where the first absorbent core layer 60 and the second absorbent core layer 70 are positioned in an offset manner and are adhesively attached, care should be taken as to how the adhesive is applied. Referring now to FIGS. 4 and 5, adhesive applied to the lower surface 60B should be strategically positioned to reduce the likelihood of contamination of the equipment. For example, as shown, adhesive applied in the front end portion 205F could contaminate the equipment as the second absorbent core layer 70 does not overly the adhesive in that area. Adhesive is needed in the central portion 205C. Additionally, adhesive should be provided in the rear end portion 205R. In such forms, adhesive would be applied to the carrier web to ensure that the second absorbent core layer 70 releases completely from the cut-and-slip or cut-and-lay operation 540B. In other forms where the end edge 76 forms the front end portion 205F, adhesive should be applied to the carrier web in the front end portion 205F and the central portion 205C to ensure that the end edge 76 is released from the cut-and-slip or cut-and-lay operation 540B. Cut-and-slip and cut-and-lay devices are well known in the art.

Referring back to FIGS. 2A-6, from the second cut-and-slip or cut-and-lay operation 530B, a laminate structure web 590 comprising the carrier web, first absorbent core 60 (including the first and second portions) and the second absorbent core 70 is provided. From here, a backsheet web, a topsheet web, and/or additional layers can be provided over the lower surface 70B of the second absorbent layer 70. The backsheet web can cover the laminate structure web 590 with or without the addition of optional layers. The backsheet web and the first or second carrier web can then be joined to encapsulate the first absorbent core layer 60 and the second absorbent core layer 70 thereby forming an absorbent article web. The absorbent article web can then be provided to a cutting device which cuts the absorbent article web into individual absorbent articles.

Figure 7:
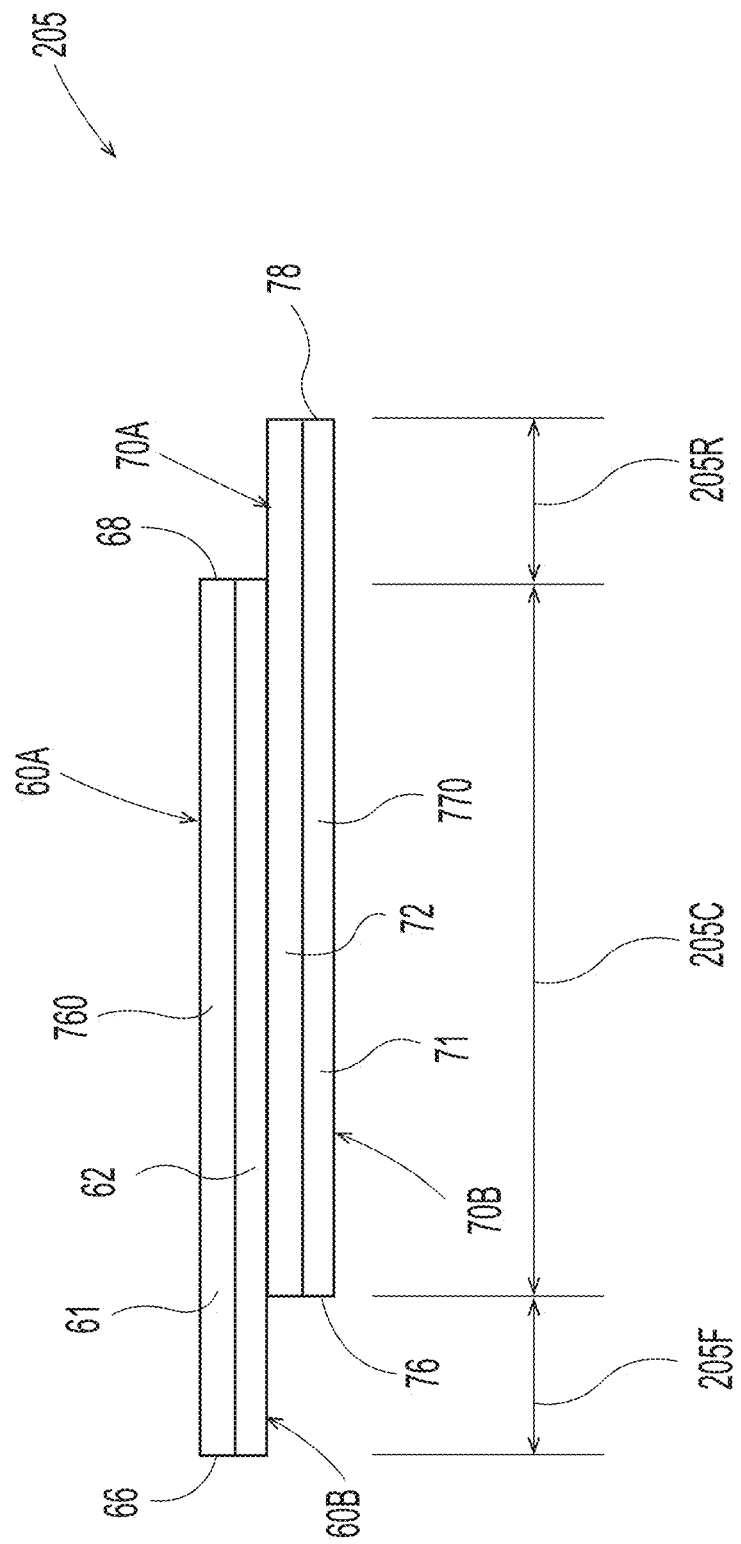
FIG. 7 is a representation of another absorbent system which is suitable for use in the absorbent articles of the present disclosure.

In some forms, the first absorbent core 60 (including the first portion and the second portion) and/or the second absorbent core 70 may comprise a plurality of webs and layers themselves. Referring now to FIG. 7, for example, the first absorbent core 60 (shown in FIGS. 2 and 4) may comprise a first superabsorbent layer 61 disposed on a first distribution layer 62, i.e. a first absorbent core laminate 760. And, the second absorbent core 70 (shown in FIGS. 3 and 4) may comprise a second superabsorbent layer 71 disposed on a second distribution layer 72, i.e. a second absorbent core laminate 770. In some forms, the first distribution layer 62 is joined to the second distribution layer 72 in an offset manner or configuration along the length of the core. This offset joinder of the first and second distribution layers 62, 72 results in an overlapping and joined area of the two laminates that forms a central portion 205C of the absorbent system 205. As shown, the front end portion 205F is formed from the end edge 66 of the first absorbent core laminate 760 while the rear end portion 205R of the core 205 is formed by the end edge 78 of the second absorbent core laminate 770. For those forms where the first distribution layer 62 is joined to the second distribution layer 72, the second absorbent core web 570 may be inverted prior to entering the cutting device 520B.

For the form of FIG. 7, the end edge 66 and end edge 78 of the first and second absorbent core laminates oppose each other and form the front end portion 205F and the rear end portion 205R of the absorbent system 205, respectively or vice versa. In other forms, the end edge 68 and end edge 76 of the first and second absorbent core laminates may oppose each other and form a front end portion 205F and a rear end portion 205R of the absorbent system 205, respectively or vice versa. In both instances, the end edge 66 and end edge 78 may be in the form of a male connection derived from a nested cut of the first and second absorbent cores. Similarly, the end edge 68 and end edge 76 may be in the form of a female connection derived from a nested cut of the first and second laminates, respectively.

In an alternate form, the first absorbent core laminate 760 may be joined to superabsorbent layer 71 instead of the second distribution layer 72. In such forms, the laminates may be joined to one another in an offset manner as well except the first distribution layer 62 is joined to the second superabsorbent layer 71 instead of the second distribution layer 72.

In some forms, the overlapping area or region that forms the central portion 205C of the core 205 has at least one characteristic of a greater capacity, a greater void volume, or a greater thickness than the front end portion 205F and the rear end portion 205F of the absorbent system 205. These forms may be particularly useful for providing for heightened leakage protection in the central portion where female users of such pads would typically contact the pad and release fluids.

Regardless of whether the absorbent system 205 utilizes the first absorbent core 60, the second absorbent core 70, the first absorbent core laminate 760, a second absorbent core laminate 770, or some combination thereof, processing of the absorbent articles of the present disclosure can be, in general, as described herein. For example, the first absorbent core laminate 760 and the second absorbent core laminate 770 can be derived from an absorbent core laminate web (including a superabsorbent layer and a distribution layer) cut in accordance with the description regarding FIGS. 2A-6. And, the webs created therefrom may then be cut as described herein and placed onto a carrier web, topsheet web, or secondary topsheet web.

Figure 8A:
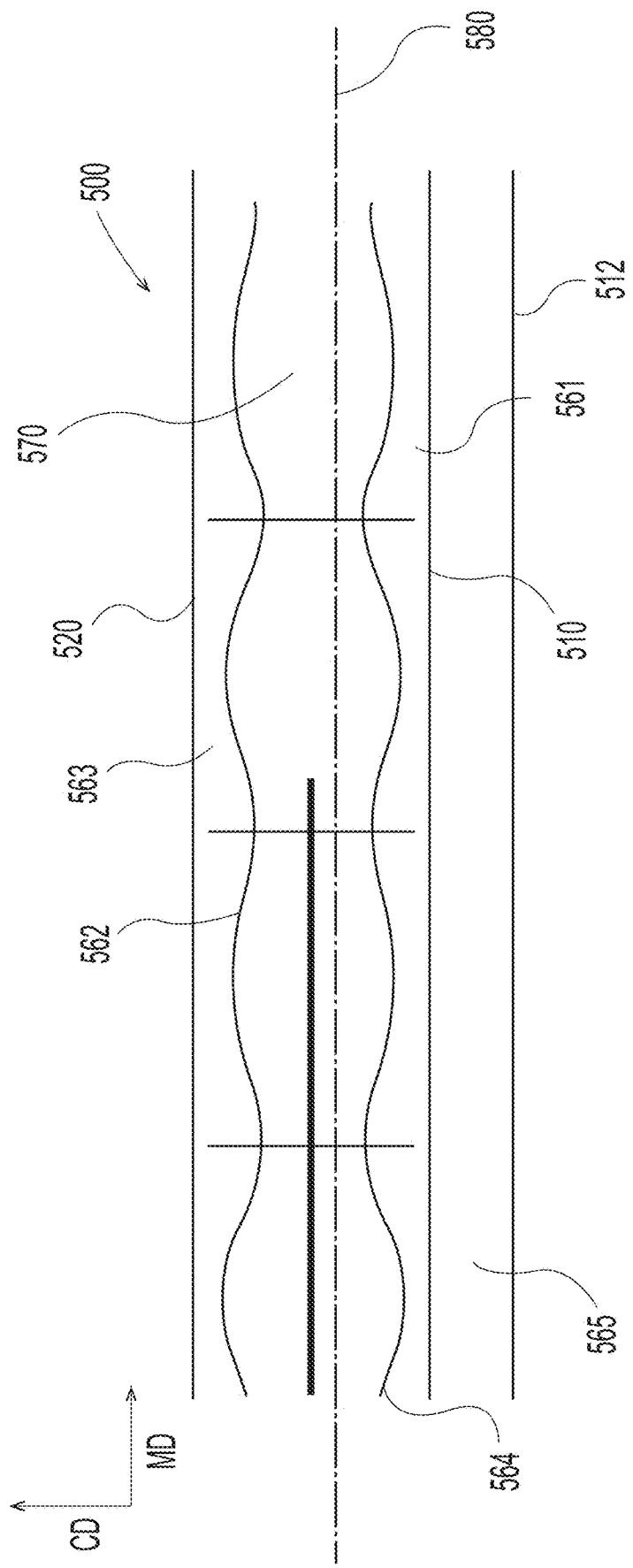
FIG. 8A is a representation of another absorbent core web with various slit lines and edges.
Figure 8B:
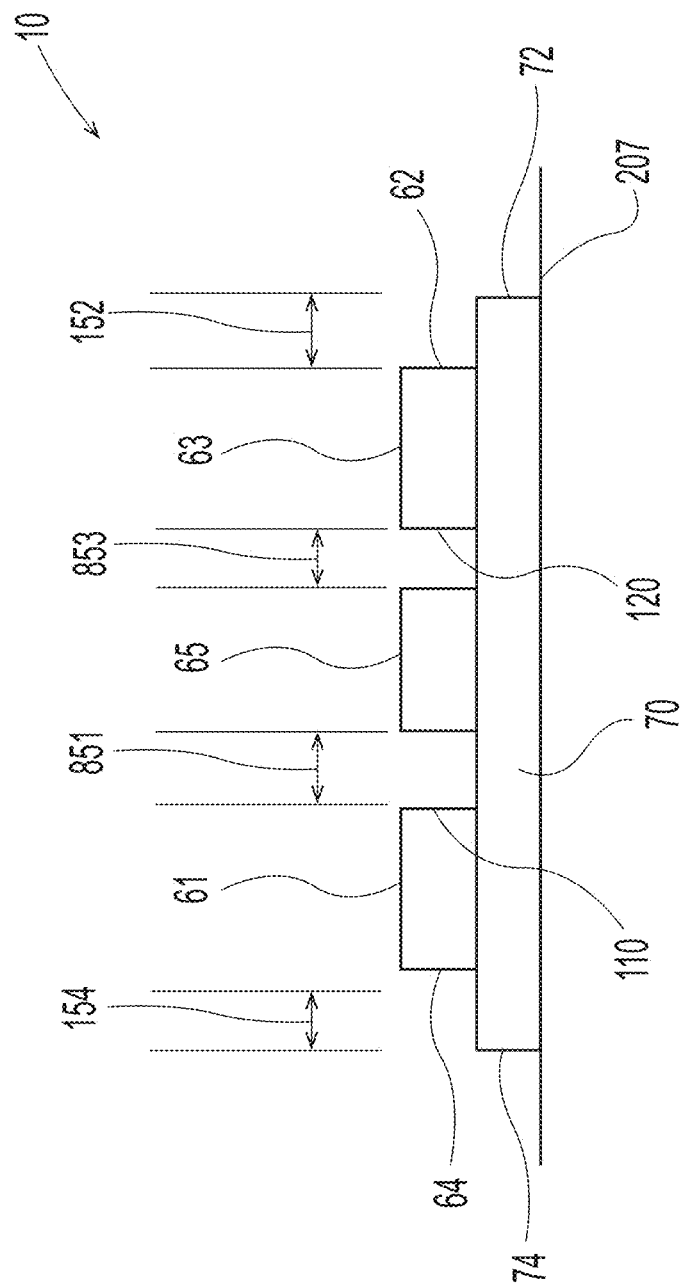
FIG. 8B is a representation of a cross section of an absorbent article constructed in accordance with the present disclosure.
Figure 9A:
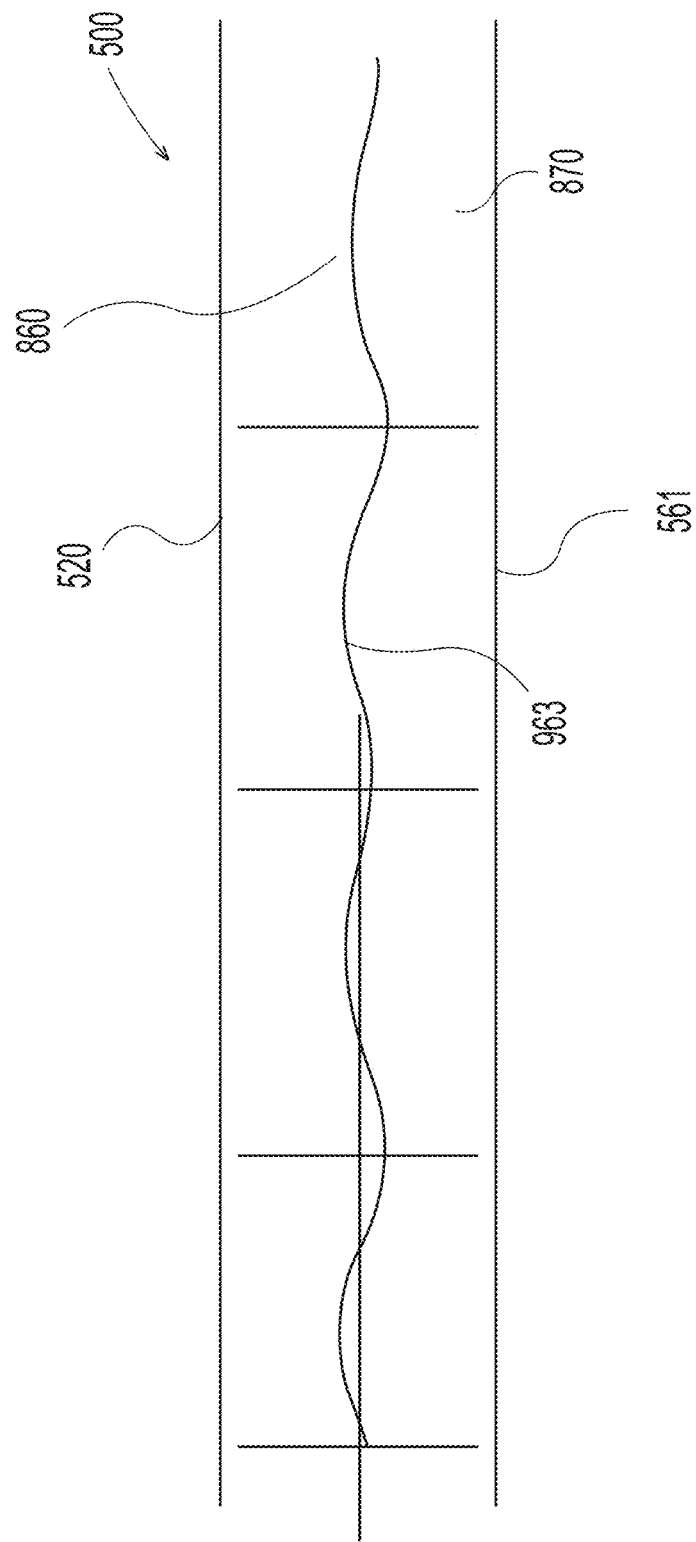
FIG. 9A is a representation of another absorbent core web with a single slit line.
Figure 9B:
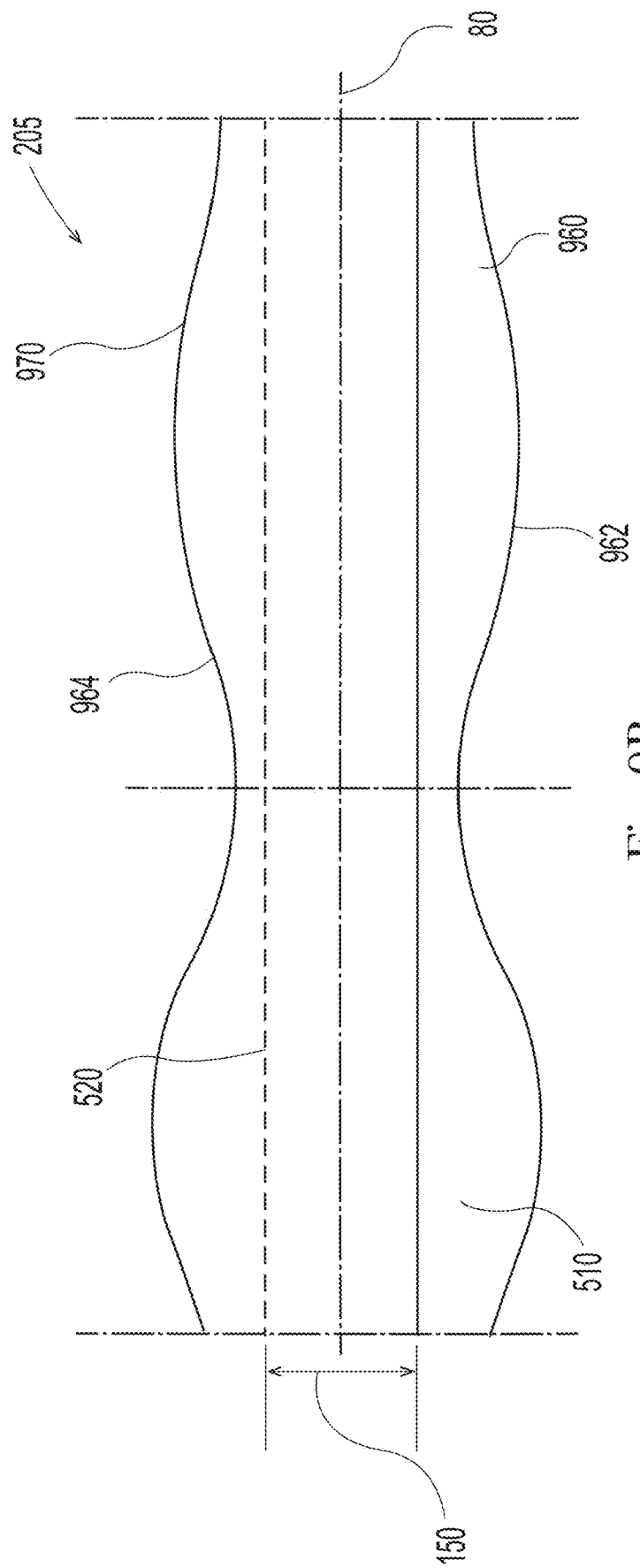
FIG. 9B is a representation of another absorbent article constructed in accordance with the present disclosure.
Figure 11:
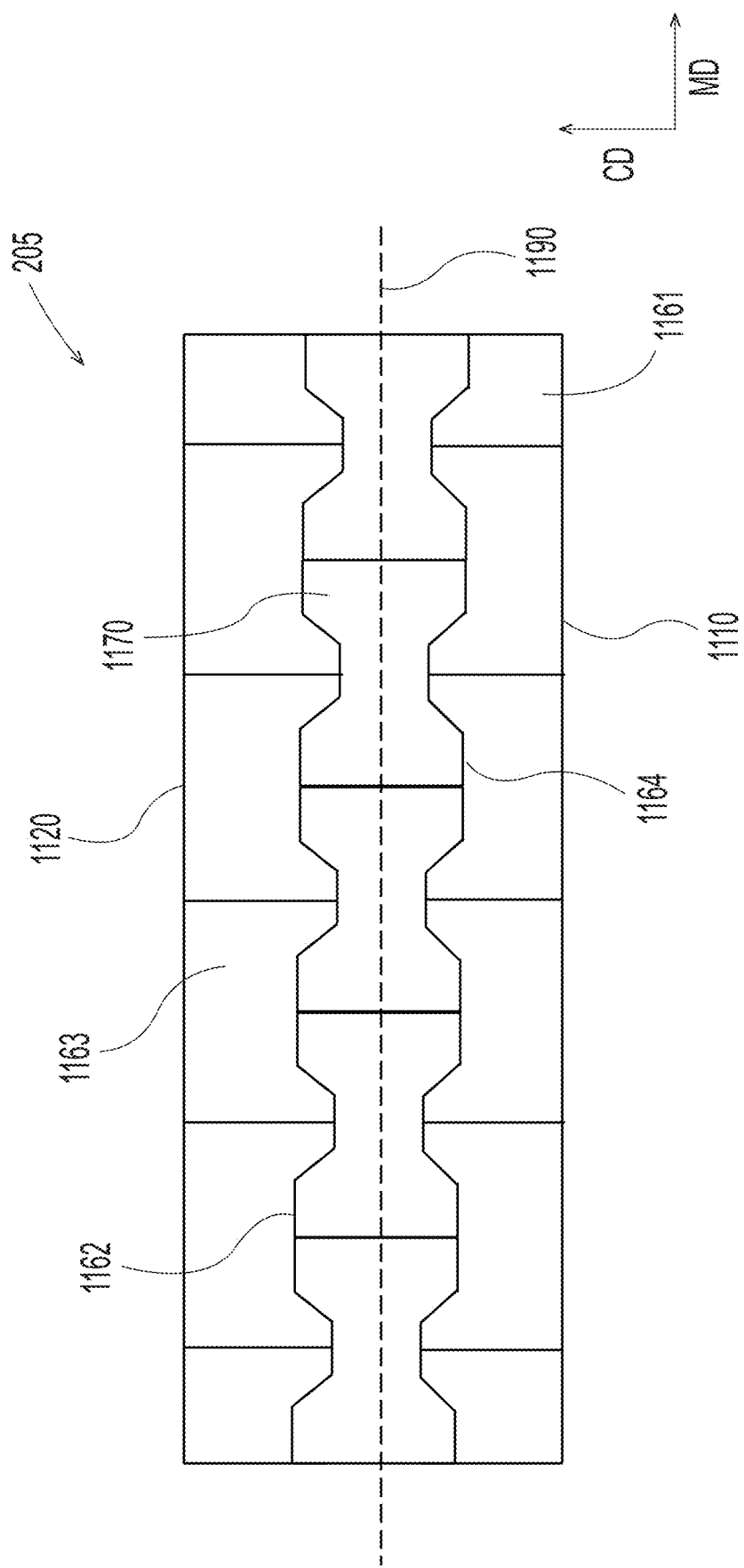

Additional forms are contemplated which can provide preferential folding of the absorbent article. Referring now to FIGS. 8A-8B, forms are contemplated where the absorbent core web 500 may be slit into four separate web streams. In such forms, in addition to the first absorbent core first portion web 561, first absorbent core second portion web 563, second absorbent core web 570, a first absorbent core third portion web 565 may be created. The first absorbent core third portion web 565 may have edges 510 and 512. As shown, the first absorbent core third portion web 565 may comprise edges 510 and 512, where edge 512 is an outer edge of the absorbent core web 500 and edge 510 is an edge formed via slitting.

Via the processing described herein, the first absorbent core third portion web 565 may be placed on the first carrier web in conjunction with the first absorbent core first portion web 561 and the first absorbent core second portion 563 webs. All three webs plus the first carrier web may then be cut by a cutting device thereby creating a plurality of discrete first absorbent cores. Each of the plurality of discrete first absorbent cores may comprise the first portion 61, the second portion 63, and a third portion 65 disposed between the first portion 61 and the second portion 63. The outboard distances 152 and 154 for this form may be as described heretofore in the first end region, intermediate region, and the second end region. Additionally, separations 851 and 852 between the first portion 61 and the third portion 65 and between the second portion 63 and the third portion 65, respectively may be as described with regard to the separation 251 shown in FIG. 2B. With the separations 851 and 852, the absorbent article 10 can have preferential bending in two specific areas across the width of the absorbent article 10. This can encourage conformance while still maintaining the required structural rigidity such that the absorbent article is not too conforming. It is worth noting that there is no requirement that the outboard distances 152, 154 disclosed herein be symmetrically distributed about the longitudinal centerline.

The conforming first absorbent and second absorbent cores may be registered such that the wider portions of the first absorbent core may coincide with wider portions of the second absorbent core. However, this is not a requirement.

Forms are contemplated where the widest portions of the first absorbent core first portion and/or second portion do not coincide with the widest portions of the second absorbent core. It is worth noting though that the width of the absorbent article along with its relative stiffness in the intermediate region should be constructed in accordance with the present description. This can allow the disposable absorbent article to compress in a pre-configured manner thereby reducing the likelihood of leakage during use.

While the discussion heretofore of the first portion 61, the second portion 63, and/or the third portion 65 have been in the context of the first absorbent core 60, these portions may similarly be utilized to construct the second absorbent core 70. Additionally, portions may be utilized in both the first absorbent core 60 and the second absorbent core 70.

Additional configurations of the absorbent system 205 are shown in FIGS. 9A-11. Regarding FIGS. 9A-9B, in some forms, the absorbent system 205 may comprise a first absorbent core 960 and a second absorbent core 970. As shown, the first absorbent core 960 and the second absorbent core 970 may be created via the absorbent core web 500. The absorbent core web 500 may be slit along line 963 to create a first absorbent core web 860 and a second absorbent core web 870. The slitting of the absorbent core web 500 as shown, can reduce the production of scrap material generated via processing of the web. For example, finished edges of the web 510 and 520 can be utilized as edges in a first absorbent core 960 and a second absorbent core 970. Additionally, contoured edges 962 and 964 of the first absorbent core 960 and the second absorbent core 970 may be created via the slit line 963. As shown, the first absorbent core 960 and the second absorbent core 970 may have the overlap distance 150 described herein.

The area of the first absorbent core 960 and the second absorbent core 970 outside of the overlap distance 150 makeup the outboard distances 152 and 154. For the forms which are constructed in accordance with FIGS. 9A-9B, the outboard distances 152 and 154 may be configured as described herein.

Another configuration of an absorbent system 205 that may be utilized with the absorbent articles of the present disclosure is shown in FIG. 10. As shown, the absorbent system 205 may comprise a first absorbent core 1060 and a second absorbent core 1070. In such forms, the second absorbent core 70 may not be present in the first end region 40. And similarly, the first absorbent core 60 may not be present in the second end region 48. Forms are contemplated where an area of the first absorbent core 60 compared to an area of the second absorbent core 70 in the first region 40 may be a ratio of about 5:1, 4:1, 3:1, 2:1, or about 1.5:1, specifically reciting all values within these ranges and any ranges created thereby. As noted previously, while the absence or at least reduced presence of the second absorbent core 70 in first end region 40 may allow for much greater flexibility in the first end region 40, due to the body contour anteriorly positioned from the vaginal opening/urethra, such conformance may not detrimentally impact the performance of the article.

Forms are contemplated where an area of the second absorbent core 70 compared to an area of the first absorbent core 60 in the second end region 48 may be a ratio of about 5:1, 4:1, 3:1, 2:1, or about 1.5:1, specifically reciting all values within these ranges and any ranges created thereby. Similar to the configuration in the first end region 40, the absence or at least reduced presence of the first absorbent core 60 in the second end region 48 may allow for much greater flexibility in the second end region 48. But, due to the body contour posteriorly positioned from the vaginal opening/urethra, such conformance may not detrimentally impact the performance of the article.

The intermediate region 44 of the absorbent system 205 may be configured as described heretofore. Namely, an overlap distance between the first absorbent core 1060 and the second absorbent core 1070 in the intermediate region 44 can be configured as described herein with regard to the overlap distance 150 (shown in FIGS. 1E-1G) in the same region. Similarly, a length of the intermediate region 44 of the absorbent system 205 of FIG. 10, can be configured as described herein.

The absorbent system 205 of FIG. 10 can be produced with the minimization or zero scrap material in mind. For example, as shown, the first absorbent core 1060 may comprise a first portion 1061 and a second portion 1063. The first portion 1061 and the second portion 1063 may be discrete and include finished edges which coincide with the longitudinal centerline 80 of the absorbent system 205. In some forms, the finished edges of the first portion 1061 and the second portion 1063 may abut one another such that there is minimal separation between the first portion 1061 and the second portion 1063. However, forms are contemplated where a separation (configured similar to the separation 251 shown in FIG. 2B) is disposed between the first portion 1061 and the second portion 1063.

Figure 11:
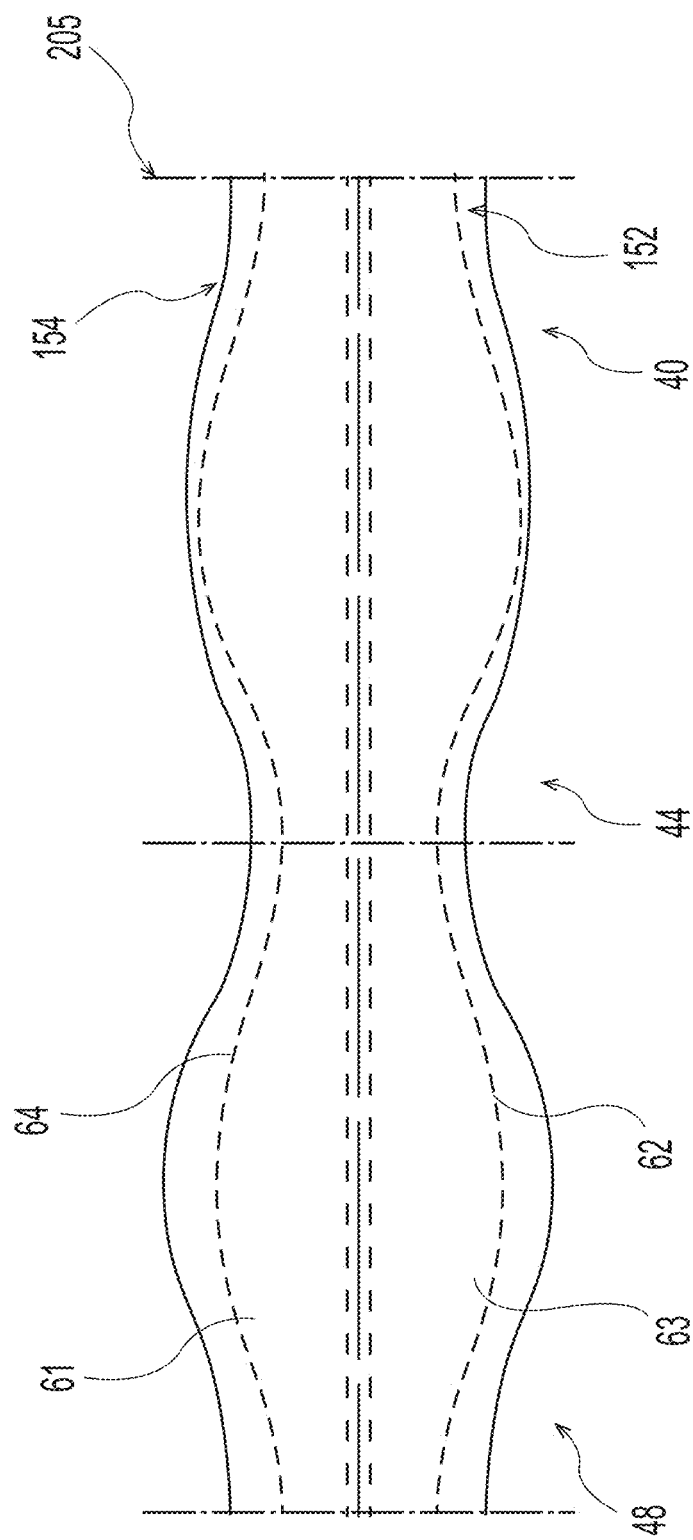
FIG. 11 is a representation of another absorbent system which is suitable for use in the absorbent article of the present disclosure.

Referring now to FIG. 11, an absorbent core web 1500 can be obtained from a supplier or can be manufactured by an absorbent article manufacturer. Similar to the process described regarding FIG. 6, the absorbent core web 1500 can be provided to a slitting machine. Slitting machines are well known in the art. As shown, the absorbent core web 1500 can be slit along slit lines 1162 and 1164 which can be offset from a longitudinal centerline 1190 of the absorbent core web 1500.

Referring now to FIGS. 2-5 and 11, post slitting, three separate webs may be created, namely, a first absorbent core first portion web 1161, a first absorbent core second portion web 1163, and a second absorbent core web 1170. The slitting of the absorbent core web 1500 can reduce the production of scrap material generated via processing of the web. For example, finished edges of the web 1110 and 1120 can be utilized in the first portion 61 and second portion 63 of the first absorbent core 60 as the first finished edge 110 and the second finished edge 120, respectively. Additionally, the edges of the first portion web 561 created by slit line 562 may be utilized in the first portion 61 of the first absorbent core 60 as side edge 62 and as side edges 72 for the second absorbent core 70. Similarly, the edges created by the slit line 1164 may be utilized by the second portion 63 of the first absorbent 60 as the side edge 64 and as the side edge 74 for the second absorbent core 70.

In some forms, the first absorbent core first portion web 1161 and the first absorbent core second portion web 1163 may then be provided to the cutting device 520A to cut discrete first portions and discrete second portions from theses absorbent core webs, respectively. Similarly, the second absorbent core web 1170 may be provided to the cutting device 520B to cut discrete second absorbent core layers from the second absorbent core web 1170. Exemplary cutting devices are known in the art. And, cutting devices for the creation of convex/concave end edges are disclosed in U.S. Patent Application Publication No. 2018/0154533.

In some forms, the cutting of the first absorbent core first portion web 561 and the first absorbent core second portion web 563 may be facilitated via the introduction of a first carrier web upstream of the cutting device 520A. In such forms, the first absorbent core first portion web 1161 and the first absorbent core second portion web 1163 can be combined with the first carrier web. The first absorbent core first portion web 1161 and the first absorbent core second portion web 1163 can be positioned on the first carrier web in their appropriate orientation, e.g. separation 251 between the first portion and second portion is provided as described herein. The first absorbent core portions and carrier web can then be provided to the cutting device simultaneously. From the cutting device a plurality of discrete first absorbent cores may be provided.

From the cutting device 520A, the plurality of discrete first absorbent core first portions is provided to the cut-and-slip or cut-and-lay operation 530A. Similarly, the first absorbent core second portions may be provided to the same cut-and-slip or cut-and-lay operation 530A as the first absorbent core first portion layers. Or in some forms, the first absorbent core second portion webs may be provided to a separate cut-and-slip or cut-and-lay operation. As noted above, where the first absorbent core first portion web 1161 and the first absorbent core second portion web 1163 are provided to the first carrier web, the plurality of discrete first absorbent cores can then be provided to a single cut-and-slip or cut-and-lay operation.

It is worth noting that where the first absorbent core layer 60 and the second absorbent core layer 70 are positioned in an offset manner and are adhesively attached, care should be taken as to how the adhesive is applied. Referring now to FIGS. 4 and 5, adhesive applied to the lower surface 60B should be strategically positioned to reduce the likelihood of contamination of the equipment. For example, as shown, adhesive applied in the front end portion 205F could contaminate the equipment as the second absorbent core layer 70 does not overly the adhesive in that area. Adhesive is needed in the central portion 205C. Additionally, adhesive should be provided in the rear end portion 205R. In such forms, adhesive would be applied to the carrier web to ensure that the second absorbent core layer 70 releases completely from the cut-and-slip or cut-and-lay operation 540B. In other forms where the end edge 76 forms the front end portion 205F, adhesive should be applied to the carrier web in the front end portion 205F and the central portion 205C to ensure that the end edge 76 is released from the cut-and-slip or cut-and-lay operation 540B. Cut-and-slip and cut-and-lay devices are well known in the art.

The absorbent core web 1500 may be processed as described with regard to FIGS. 2-6. Additionally, the absorbent core web 1500 may be processed such that it comprises a configuration which is described with regard to the absorbent cores and/or absorbent systems described herein.

Applicant shall now provide more detailed insight into the individual components of the disposable absorbent articles envisioned herein.

Primary Topsheet

Referring back to FIGS. 3-4, the primary topsheet 203 (also referred to herein "topsheet") of the chassis 20 is positioned adjacent a body-facing surface 203A of the absorbent system 205 and may be joined thereto and to the backsheet 207 by attachment methods (not shown) such as those well known in the art. Suitable attachment methods are described with respect to joining the backsheet 207 to the absorbent system 205. The topsheet 203 and the backsheet 207 may be joined directly to each other in the incontinence pad periphery and may be indirectly joined together by directly joining them to the absorbent system 205 or additional optional layers within the chassis like a secondary topsheet which spans the entire or partial area of the article. This indirect or direct joining may be accomplished by attachment methods which are well known in the art.

The absorbent article may comprise any known or otherwise effective primary topsheet, such as one which is compliant, soft feeling, and non-irritating to the wearer's skin. Suitable primary topsheet materials include a liquid pervious material that is oriented towards and contacts the body of the wearer permitting bodily discharges to rapidly penetrate through it without allowing fluid to flow back through the topsheet to the skin of the wearer. The primary topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof. Some suitable examples of films that can be utilized as topsheets are described in U.S. Pat. Nos. 3,929,135; 4,324,246; 4,342,314; 4,463,045; 5,006,394; 4,609,518; and 4,629,643.

Nonlimiting examples of woven and nonwoven materials suitable for use as the topsheet include fibrous materials made from natural fibers, modified natural fibers, synthetic fibers, or combinations thereof. Some suitable examples are described in U.S. Pat. Nos. 4,950,264, 4,988,344; 4,988,345; 3,978,185; 7,785,690; 7,838,099; 5,792,404; and 5,665,452.

In some forms, the topsheet may comprise tufts as described in U.S. Pat. Nos. 8,728,049; 7,553,532; 7,172,801; 8,440,286; 7,648,752; and 7,410,683. The primary topsheet may have a pattern of discrete hair-like fibrils as described in U.S. Pat. No. 7,655,176 or 7,402,723. Additional examples of suitable topsheet includes those described in U.S. Pat. Nos. 8,614,365; 8,704,036; 6,025,535 and in U.S. Patent Application Publication Nos 13743M.

Another suitable primary topsheet or a primary topsheet combined with a secondary topsheet may be formed from a three-dimensional substrate as detailed in a U.S. Patent Application Publication No. 2017/0258647 A1.

The primary topsheet may have one or more layers, as described in U.S. Patent Application Publication Nos. 2016/0167334 A1; 2016/0166443 A1; 2017/0258651 A1. The topsheet may be apertured as disclosed in U.S. Pat. No. 5,628,097, to Benson et al., issued on May 13, 1997.

Secondary Topsheet

As noted previously, the disposable absorbent articles of the present disclosure may comprise additional layers, one of which includes a secondary topsheet. As mentioned previously, the secondary topsheet may be separate and apart from the absorbent system. Additionally, the secondary topsheet is disposed beneath the primary topsheet 203 and on the body-facing surface of the core. In some forms, the secondary topsheet may have a basis weight from about 40 gsm to about 100 gsm, from about 45 gsm to about 75 gsm, or from about 50 gsm to about 60 gsm, specifically including all values within these ranges and any ranges created thereby. In some forms, the secondary topsheet may comprise a homogeneous mix of fibers.

Some exemplary secondary topsheets are described in U.S. Patent Application Publication Nos. 2015/0351976 A1 and 2014/0343523 A1; and U.S. Patent Application Publication No. 2018/0098893. Forms are contemplated where the carrier web comprises a secondary topsheet.

Backsheet

The backsheet 207 of the chassis 20 may be positioned adjacent a garment-facing surface of the absorbent system 205 and may be joined thereto by attachment methods (not shown) such as those well known in the art. For example, the backsheet 207 may be secured to the absorbent system 205 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent system 205 is not joined to the backsheet 207, the topsheet 203, or both.

The backsheet 207 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent system 205 from wetting articles of clothing which contact the incontinence pad 10 such as undergarments. However, in some instances, the backsheet 207 may permit vapors to escape from the absorbent system 205 (i.e., is breathable) while in other instances the backsheet 207 may not permit vapors to escape (i.e., non-breathable). Thus, the backsheet 205 may comprise a polymeric film such as thermoplastic films of polyethylene or polypropylene. A suitable material for the backsheet 207 is a thermoplastic film having a thickness of from about 0.012 mm (0.5 mil) to about 0.051 mm (2.0 mils), for example. Any suitable backsheet known in the art may be utilized with the present invention.

Some suitable examples of backsheets are described in U.S. Pat. Nos. 5,885,265; 4,342,314; and 4,463,045. Suitable single layer breathable backsheets for use herein include those described for example in GB A 2184 389, GB A 2184 390, GB A 2184 391, U.S. Pat. Nos. 4,591,523, 3,989,867, 3,156,242; WO 97/24097 and U.S. Pat. Nos. 6,623,464; 6,664,439 and 6,436,508.

The backsheet may have two layers: a first layer comprising a gas permeable aperture formed film layer and a second layer comprising a breathable microporous film layer as described in U.S. Pat. No. 6,462,251. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Absorbent System

The absorbent system 205 of the present invention may comprise any suitable shape. As noted previously, as the absorbent system 205 is typically the stiffest portion of the absorbent article. So, shapes which are useful for the articles of the present disclosure, will typically comprise a reduced width intermediate region. For example, in some forms of the present invention, the absorbent system 205 may comprise a contoured shape, e.g. narrower in the intermediate region than in the end regions. As yet another example, the absorbent system may comprise a tapered shape having a wider portion in one end region of the pad which tapers to a narrower intermediate and end region in the other end region of the pad. The absorbent system 205 may comprise varying stiffness in the MD and CD.

As detailed earlier, the absorbent system 205 comprises the first absorbent core and the second absorbent core. And as described herein the first absorbent core and/or the second absorbent core may comprise a single layer or multiple layers. Both are generally compressible, conformable, non-irritating to the wearer's skin, and capable of absorbing and retaining liquids such as urine and other certain body exudates including menses.

The configuration and construction of the absorbent system 205 may vary (e.g., the absorbent system 205 may have varying caliper zones, a hydrophilic gradient, a superabsorbent gradient, or lower average density and lower average basis weight acquisition zones). Further, the size and absorbent capacity of the absorbent system 205 may also be varied to accommodate a variety of wearers. However, the total absorbent capacity of the absorbent system 205 should be compatible with the design loading and the intended use of the disposable absorbent article or incontinence pad 10.

In some forms of the present disclosure, the absorbent system 205 may comprise a plurality of multi-functional layers that are in addition to the first and second absorbent cores. For example, the absorbent system 205 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent system 205 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066; WO 95/11652; U.S. Pat. Publ. No. 2008/0312622A1; and WO 2012/052172. These may be used to configure the superabsorbent layers.

Additions to the core of the present disclosure are envisioned. In particular, potential additions to the current multi-laminate absorbent core are described in U.S. Pat. Nos. 4,610,678; 4,673,402; 4,888,231; 4,834,735; 5,234,423; and 5,147,345. These are useful to the extent they do not negate or conflict with the effects of the below described layers of the absorbent core of the present invention.

The first and second absorbent cores layers and/or laminates of the absorbent system 205 have been detailed earlier but it is important to note that these layers or laminates may have cross-direction widths that are the same as each other or different. As discussed previously, for example, the first absorbent core layer or laminate may have a lesser cross-direction width than said second absorbent core layer or laminate or a greater cross-direction width than said second absorbent core layer or laminate. In certain instances, the first and second absorbent core layers or laminates can have machine-direction lengths that are the same while in other instances, the first and second absorbent cores have machine-direction lengths that are different. In the latter instance, the first absorbent core layer or laminate may have a lesser machine-direction length than the second absorbent core layer or laminate, or conversely the first absorbent core layer or laminate may have a greater machine-direction length than said second absorbent core layer or laminate.

The first and second absorbent core layers or laminates in some forms, may further comprise an optional intermediate layer disposed between the respective superabsorbent layer and distribution layer. This optional intermediate layer may comprise materials detailed herein relative to the optional layers for the chassis, in general.

Additionally, in some forms, in addition to the first and second absorbent cores layers or laminates, the absorbent article or incontinence pad may further comprise an optional additional absorbent core comprising a superabsorbent layer and/or a distribution layer. This optional additional core may take the form of a third, fourth, fifth, or even additional layers. The superabsorbent layer and distribution layer may exhibit the same or different properties detailed earlier with respect to the first and second superabsorbent and distribution layers. Any optional additional cores may be disposed on a body-facing surface of the first absorbent core or second absorbent core or on a garment-facing surface of the first absorbent core or second absorbent core.

As stated previously, in some forms, the first absorbent core layer or laminate has end edge 66 that is complementary in shape to its respective end edge 68. More specifically, the end edge 66 of the first absorbent core layer or laminate may conform shapewise to the end edge 68 of the same. The same conformance may apply to the second absorbent core layer or laminate. This conformation results from a nested cut of the first absorbent core layer or laminate and the second absorbent core layer or laminate that provides matching or shape fitting ends. Likewise, this feature may also be prevalent in any optional absorbent cores that might be incorporated into the absorbent system. This nesting or nested cut feature of the absorbent cores allow for reduced waste of trim during manufacture. It has also been found that it is possible to configure the first and second absorbent core layers or laminates in a manner that allows for their respective convex edges to oppose one another when the first and second layers are overlapped and joined forming an absorbent system with a central portion 205C comprising an overlapping area.

Referring to FIGS. 4 and 7, as noted previously, the front end portion of the absorbent system 205F can be formed from end edge 66 or end edge 78 of either the first absorbent core or the second absorbent core. A rear end portion of the absorbent system 205R is similarly formed from end edge 66 or end edge 78 of the other of the first absorbent core or the second absorbent core. This configuration yields an absorbent system with matching (i.e., a male connection) ends. In other forms, a front end portion of the absorbent system may be formed from end edge 66 or end edge 76 of either the first absorbent core or the second absorbent core while the rear end portion of the absorbent system is formed from end edge 68 or end edge 78 of the other of the first absorbent core or second absorbent core. In such forms, the second end is shaped as a female connection and therefore does not match the front end portion of the same core. In other forms, the front end portion of the absorbent system may be formed from the end edge 68 of the first absorbent core or end edge 78 of the second absorbent core. A rear end portion of the absorbent system may be similarly formed from the end edge 68 of the remaining first absorbent core or the end edge 78 of the second absorbent core. This configuration yields an absorbent system with matching (i.e., a female connection) ends. It should be noted, however, that the width of the first and second absorbent cores may be the same or different as mentioned herein. The nested cuts of the end edges of each of the first and second absorbent cores can have shapes selected from the group consisting of arcs, semicircles, semi-ellipses, chevrons, rectangles, sinusoids, jigsaws, and combinations thereof.

In some forms, the first or second absorbent cores may include one or more recessed areas that run along the machine direction or cross direction. These recessed areas may coincide with the discontinuous patterns of one or more of a superabsorbent layer and distribution layer, whether it be of the first absorbent core, second absorbent core, or both. These recessed areas may also merely be formed by embossing of the first or second absorbent cores. These recessed areas may alternatively be formed by slitting, cutting, ring-rolling, or otherwise providing mechanical deformation through the first and/or second absorbent cores. Each manner of recessed area formation mentioned herein is intended to yield a recessed area that is capable of providing a point of preferential bending of the overall article.

Additionally, for those forms where the first absorbent core and/or the second absorbent core do not comprise laminate structures, an airlaid core material can be utilized. Any suitable airlaid core can be utilized. Airlaid core material can be obtained by a manufacturer of such materials or can be made online via equipment known in the art. Where an airlaid core is utilized, the need for separate superabsorbent layers and distribution layers may be reduced. In such forms, the absorbent core web 500 (shown in FIG. 5) may comprise an airlaid web as described herein. Suitable airlaid absorbent core structures are disclosed in U.S. Pat. Nos. 8,105,301 and 8,603,622 and U.S. Patent Application No. 2017/0348166.

Superabsorbent Layers

Referring to FIG. 7, the first and second superabsorbent layers 61, 71 of the first and second absorbent core laminates 760, 770 comprise superabsorbent polymers or absorbent gelling materials (AGM). In some forms, the superabsorbent layer 61 and/or 71 may comprise the carrier web and composition. In such forms, superabsorbent may be deposited on the carrier web to form the superabsorbent layers. The superabsorbent layers may comprise AGM particles or AGM fibers. In general, such AGM's have been used only for their fluid-absorbing properties. Such materials form hydrogels on contact with liquid (e.g., with urine, blood, and the like). One highly preferred type of hydrogel-forming, absorbent gelling material is based on the hydrolyzed polyacids, especially neutralized polyacrylic acid. Hydrogel-forming polymeric materials of this type are those which, upon contact with fluids (i.e., liquids) such as water or body fluids, imbibe such fluids and thereby form hydrogels. In this manner, fluid discharged into the fluid absorbent structures herein can be acquired and held. These preferred superabsorbent polymers will generally comprise substantially water-insoluble, slightly cross-linked, partially neutralized, hydrogel-forming polymer materials prepared from polymerizable, unsaturated, acid-containing monomers.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles.

In some forms, the absorbent cores or portions thereof of the present disclosure may be substantially free of airfelt and are thus distinct from mixed layers that may include airfelt. As used herein, "substantially free of airfelt" means less than 5%, 3%, 1%, or even 0.5% of airfelt. In some forms, there may be no measurable airfelt in the superabsorbent layers. In the case of the first superabsorbent layer, it is preferably disposed onto the first distribution layer discontinuously. And as noted previously, the second superabsorbent layer may, in conjunction with the first superabsorbent layer or independently thereof, be disposed on the second distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

In some forms, the first and second superabsorbent layers may comprise superabsorbent polymers that are the same. In other embodiments, the first and second superabsorbent layers may comprise superabsorbent polymers that are different from one another. This may be in addition to the different deposition patterns that are discussed above.

The superabsorbent layers are disposed having a thickness of 0.2 mm, 0.3 mm, 0.4 mm, or 0.5 mm to 1 mm, 1.2 mm, 1.4 mm, 1.8 mm, or 2 mm. The first and second superabsorbent layers may have the same or different cross-direction widths as applied to their respective distribution layers. For instance, the cross-direction widths of the first and second superabsorbent layers may be from 20 mm, 25 mm, 30 mm, 35 mm, or 40 mm to 50 mm, 60 mm, 65 mm, 70 mm, 80 mm, or 90 mm. Alternatively, in embodiments where the widths of the first and second superabsorbent layers differ from one another in the cross-direction width, the first superabsorbent layer may have a lesser cross-direction width than the second superabsorbent layer. In particular, the first superabsorbent layer may have a cross-direction width that is less than about 95%, 90%, 80%, 70%, or even 60% of the width of the second superabsorbent layer.

In certain embodiments, the one or both of the first and second superabsorbent layers span greater than greater than about 50%, 60%, 70%, 80%, 90%, or even 95% of the cross-direction width of a superabsorbent carrier layer and/or the respective adjoining first or second distribution layer. Forms of the present disclosure are contemplated where the absorbent core web 500 comprises a superabsorbent layer which is processed to form the superabsorbent layer 61 and superabsorbent layer 71.

Carrier Webs/Optional Layers

Recall that carrier webs may comprise the primary topsheet and/or the secondary topsheet. And, like the optional layers that may be included in the chassis, the absorbent system may also comprise similar optional layers. The following descriptions and attributes of the optional layers are also suitable for use in the carrier web. For the sake of facility, the term "webs" shall encompass the optional layers as well as the carrier webs. The optional layers and/or carrier webs may be webs selected from the group consisting of a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

These optional layers and/or carrier webs may comprise materials such as creped cellulose wadding, fluffed cellulose fibers, airfelt, and textile fibers. The materials of the webs may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The optional layers may be any combination of the materials listed above and/or a plurality of the materials listed above, alone or in combination.

The materials of the webs may be hydrophobic or hydrophilic depending on their placement within the chassis.

The materials of the webs may comprise constituent fibers comprising polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a superabsorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e., capillary and round) and the like. The constituent fibers may range from about 0.1 denier to about 100 denier.

The webs may include thermoplastic particulates or fibers. The materials, and in particular thermoplastic fibers, may be made from a variety of thermoplastic polymers including polyolefins such as polyethylene (e.g., PULPEX™) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse™ by Glyco Chemical, Inc. of Greenwich, Conn. Besides nonionic surfactants, anionic surfactants may also be used. These surfactants may be applied to the thermoplastic fibers at levels of, for example, from about 0.2 to about 1 $g/cm^2$ of thermoplastic fiber.

Suitable thermoplastic fibers may be made from a single polymer (monocomponent fibers) or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the webs of this disclosure may include sheath/core fibers having the following polymer combinations: polyethylene/polypropylene, polyethyl vinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON™, CELBOND™, or CHISSO™ bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e., unbent) or crimped (i.e., bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties—of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The webs may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON™, and KODEL™), high melting crimped polyester fibers (e.g., KODEL™ 431 made by Eastman Chemical Co.) hydrophilic nylon (HYDROFIL™), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

Distribution Layers

The first and second distribution layers are useful for wicking bodily fluids away from the skin of a wearer to facilitate comfort of continued wear after a release. In some forms, the support web may comprise the distribution layer. In some forms, the support web may be configured similar to the carrier web described herein. In some forms, the first and second distribution layers of the first and/or second laminates not only face one another but are joined in an offset manner to form part of the core. The distribution layers comprise one or more of cellulose and commuted wood pulp. This may be in the form of airlaid. The airlaid may be chemically or thermally bonded. In particular, the airlaid may be multi bonded airlaid (MBAL). In this instance, the distribution layer may further comprise a fibrous thermoplastic adhesive material at least partially bonding the airlaid to itself and adjacent distribution layers, superabsorbent layers, or other additional (optional) layers. It should be noted that the same materials that are suitable for the optional layers of the chassis are envisioned as suitable for use in the distribution layers. The basis weight for each of the first and second distribution layers range from 80 gsm, 80 gsm, 100 gsm, 110 gsm, 120 gsm, or 130 gsm to 140 gsm, 150 gsm, 160 gsm, 180 gsm, 200 gsm, 220 gsm, or 240 gsm. A preferred basis weight is 135 gsm for each of the distribution layers of the first and second laminates. Forms are contemplated where the absorbent core web 500 (shown in FIG. 5) comprises a laminate structure of a superabsorbent layer and a distribution layer.

Barrier Cuffs

Referring back to FIG. 3, the incontinence pad 10 may further comprise a first barrier cuff 230A and a second barrier cuff 230B and fastening adhesive 211 disposed on the garment-facing surface 20B of the chassis 20. As shown, the fastening adhesive 211 may not extend out laterally to the same extent as the absorbent system 205. As such, constructions where pad curl is reduced would be beneficial.

The first barrier cuff 230A and the second barrier cuff 230B may be attached to the chassis 20 in any suitable location. For example, as shown, the first barrier cuff 230A and the second barrier cuff 230B may be attached to a wearer-facing surface 20A of the chassis 20. As shown, the first barrier cuff 230A and the second barrier cuff 230B are attached to the primary topsheet 203. In some forms, the first barrier cuff 230A and the second barrier cuff 230B may be attached to a garment-facing surface 20B of the chassis 20. For example, the first barrier cuff 230A and the second barrier cuff 230B may be attached to the backsheet 207. Some examples of other suitable barrier cuffs are described in U.S. Pat. Nos. 4,695,278; 4,704,115; 4,795,454; 4,909,803; U.S. Patent Application Publication No. 2009/0312730.

As shown, in some forms, the first barrier cuff 230A comprises a first cover 231 and a first elastic member 233.

The second barrier cuff 230B comprises a second cover 235 and a second elastic member 237. As shown, the first cover 231 may fully enclose the first elastic member 233. Similarly, the second cover 235 may fully enclose the second elastic member 237.

While the first barrier cuff 230A and the second barrier cuff 230B are shown as discrete elements which are attached to the chassis 20, any suitable configuration may be utilized. For example, the first cover 231 and/or the second cover 235 may comprise a portion of the primary topsheet 203 and/or a portion of the backsheet 207. In such forms, the first barrier cuff 230A and/or the second barrier cuff 230B may be integrally formed with the chassis 20. A form where the first barrier cuff 230A and the second barrier cuff 230B are integrally formed with the chassis 20 is shown in FIG. 3 and discussed hereafter.

The first elastic member 233 and the second elastic member 237 may be attached to the first cover 231 and the second cover 235, respectively, by any suitable means. In one example, the first elastic member may be adhesively attached to the first cover 231. Similarly, the second elastic member 237 may be adhesively attached to the second cover 235. For example, as shown, first adhesive portions 251 and 253 may attach the elastic members 233 and 237 to their respective covers 231 and 235. Similarly, second adhesive portions 255 and 257 may attach their respective covers 231 and 235 to the primary topsheet 203. As described below, the first elastic member 233 and the second elastic member 237 may be attached in only a portion the first cover 231 and second cover 235, respectively. Additional forms are contemplated where the first elastic member 233 and/or the second elastic member 237 are attached to the chassis 20 in conjunction with or independently from their respective covers 231 and 235.

Referring to FIG. 3, the elastic members 233 and 237 may be disposed laterally inboard of side edges 205A and 205B of the absorbent system 205. In other forms, the elastic members 233 and 237 may be disposed laterally outboard of the side edges 205A and 205B of the absorbent system 205. Still in other forms, the elastic members 233 and 237 may be disposed laterally inboard of the side edges 205A and 205B of the absorbent system 205 in the first end region 40 and the second end region 48 but laterally outboard of side edges 205A and 205B of the absorbent system 205 in the intermediate region 44. Additional forms are contemplated where the elastic members 233 and 237 are disposed laterally inboard of the side edges 205A and 205B of the absorbent system 205 in the first end region 40 but are disposed outboard of the side edges 205A and 205B of the absorbent system 205 in the intermediate region 44 and/or the second end region 48.

The elastic members comprised by the barrier cuffs can be glued in, in various glue lengths using various glues and glue amounts and placements. Placement of the glue is yet another variable which should be considered especially when designed with the core flexibility in mind. Gluing of the elastic members and the covers create anchor points on the pad.

The covers of the barrier cuffs of the present invention can be made of varying types of nonwovens of different MD and CD flexibility. The cover can be bonded to the topsheet of the absorbent article, such as, for example, by a slot coated stripe of adhesive, glue beads, ultrasonic sealing, or other suitable bonding agents. In certain forms of the present invention, the cover can be bonded to the backsheet at the side edges 22 and 24 (see FIG. 1) of the pad, such as, for example, using a crimp or other suitable bonding agents, such as, for example, adhesive.

Elastic members may comprise any suitable elastic material. Some suitable examples include Spandex™ or other similar polyurethanes, natural or synthetic rubber, styrene block copolymers, metallocene polyolefins, Lycra™, or any other suitable elastomer materials known in the art. Preferably the elastic member is durable for ease of processing and for during the use of the article and exhibits excellent elasticity (recovery after strain) even under strains as high as 400%.

Additionally, the elastic members of the present disclosure may comprise any suitable dtex. In other forms, the elastic members may comprise a dtex of 680 or less. In some forms, the elastic members may have a dtex between 680 and 470, specifically including all numbers within the range and any ranges created thereby.

Minimum spacing between the first barrier cuff 230A and the second barrier cuff 230B may be largely driven by female anatomy. However, tradeoffs can occur where the barrier cuffs (and their respective elastic members) are disposed too far outboard of the absorbent system 205 and too far inboard of the absorbent system 205. As such, spacing between the most distal elastic members of their respective barrier cuffs should be carefully selected. Starting from the narrowest width, spacing between the most distal elastic members of the first barrier cuff 230A and the second barrier cuff 230B should be large enough to allow sufficient access to the absorbent system 205 during use while also taking into account the forces which will be applied to the pad. If too narrow, access to a portion of the absorbent system 205 could be obstructed which could lead to leakage despite the barrier cuffs 230A and 230B. In some forms of the present invention, minimum spacing between the elastic member of the first barrier cuff 230A and the elastic member of the second barrier cuff 230B which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Test Methods

Linear Distances

Linear distances may be measured by any appropriate instrument that is calibrated and capable of a measurement to the nearest 0.1 mm. Area measurements are made using the projected area of the article, as viewed orthogonally to the plane of the longitudinal and transverse axes, in square millimeters to the nearest 0.1 $mm^2$.

Caliper

The caliper, or thickness, of a material is measured as the distance between a reference platform on which the material rests and a pressure foot that exerts a specified amount of pressure onto the material over a specified amount of time. All measurements are performed in a laboratory maintained at 23° C.±2° C. and 50%±2% relative humidity and test samples are conditioned in this environment for at least 2 hours prior to testing.

Caliper is measured with a manually-operated micrometer equipped with a pressure foot capable of exerting a steady pressure of 0.50 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter that is smaller than the test sample and capable of exerting the required pressure. A suitable pressure foot has a diameter of 56 mm, however a smaller or larger foot can be used depending on the size of the sample being measured. The test sample is supported by a horizontal flat reference platform that is larger than and parallel to the surface of the pressure foot. The system is calibrated and operated per the manufacturer's instructions.

Obtain a test sample by removing it from an absorbent article, if necessary. When excising the test sample from an absorbent article, use care to not impart any contamination or distortion to the test sample layer during the process. The test sample is obtained from an area free of folds or wrinkles, and it must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm±1.0 mm per second until the full pressure is exerted onto the test sample. Wait 5 seconds and then record the caliper of the test sample to the nearest 0.01 mm. In like fashion, repeat for a total of five replicate test samples. Calculate the arithmetic mean for all caliper measurements and report as Thickness to the nearest 0.01 mm.

Intermediate Zone Test Method

The Intermediate Zone Test Method is used to determine the intermediate zone length index value and the transverse width of a shaped core at multiple characteristic points.

A two-dimensional shape, defined by the projection of a planar core perpendicular to both its longitudinal and transverse axes, is captured and is hereafter referred to as the core projection. The core projection retains the same longitudinal and transverse axes of the core itself. The centroid of the core projection is calculated, and the position of the centroid along the longitudinal axis of the core projection is defined as the core centroid point. A line extending through the core centroid point and parallel to the transverse axis is used to partition the core projection into two sub-shapes, a first core projection and a second core projection. The centroids of the first core projection and second core projection are calculated and defined as the first centroid and second centroid, respectively. The position of the first centroid along the longitudinal axis of the core projection is defined as the first core centroid point. The position of the second centroid along the longitudinal axis of the core projection is defined as the second core centroid point.

Lines extending through the first and second centroid points parallel to the transverse axis of the core projection delineate the front and rear boundaries of the intermediate zone. The length of the intermediate zone along the longitudinal axis is calculated and reported to the nearest 0.1 mm.

The intermediate zone length index value is calculated by dividing the length of the intermediate zone by the total length of the core projection along the longitudinal axis and is a dimensionless ratio reported to the nearest 0.01.

The transverse width of the core projection is measured at the front centroid point and rear centroid point and each is reported to the nearest 0.1 mm. The transverse width of the core projection is measured at the narrowest point within the intermediate zone and reported to the nearest 0.1 mm.

All measures are performed on five substantially similar absorbent cores and reported as the arithmetic mean of the five values.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin having a longitudinal centerline and a lateral centerline generally perpendicular to the longitudinal centerline, the sanitary napkin comprising:
    a topsheet;
    a backsheet;
    a first end region, an opposing second end region and an intermediate region disposed between the first end region and the second end region;
    a first absorbent layer disposed between the topsheet and the backsheet, the first absorbent layer having a first end region first absorbent layer width, an intermediate region first absorbent layer width measured along the lateral centerline, and a second end region first absorbent layer width;
    a second absorbent layer disposed between the first absorbent layer and the backsheet, the second absorbent layer having a first end region second absorbent layer width, an intermediate region second absorbent layer width measured along the lateral centerline, and a second end region second absorbent layer width,
    wherein the respective widths have the following relationships:
        the first end region first absorbent layer width is greater than the second end region first absorbent layer width, and the second end region first absorbent layer width is greater than the intermediate region first absorbent layer width, and
        the first end region second absorbent layer width is greater than the second end region second absorbent layer width, and the second end region second absorbent layer width is greater than the intermediate region second absorbent layer width, wherein the first absorbent layer comprises a first end edge and an opposing second end edge, wherein the second absorbent layer comprises a first end edge and an opposing second end edge, and wherein the first end edge of the first absorbent layer is coterminous with the first end edge of the second absorbent layer or the second end edge of the first absorbent layer is coterminous with the second end edge of the second absorbent layer.

2. The sanitary napkin of claim 1, wherein the first end region second absorbent layer width is greater than the first end region first absorbent layer width.

3. The sanitary napkin of claim 2, wherein the second absorbent layer in the first end region extends outboard of the first absorbent layer in the first end region by a first end region outboard distance.

4. The sanitary napkin of claim 3, wherein the second absorbent layer in the intermediate region extends outboard of the first absorbent layer in the intermediate region by an intermediate region outboard distance.

5. The sanitary napkin of claim 1, wherein the intermediate region first absorbent layer width is less than the intermediate region second absorbent layer width.

6. The sanitary napkin of claim 5, wherein a first end region outboard distance is less than an intermediate region outboard distance.

7. The sanitary napkin of claim 6, wherein the intermediate region outboard distance is between about 5 mm and about 20 mm.

8. The sanitary napkin of claim 1, wherein the first absorbent layer comprises a first portion, a second portion, and a separation disposed between the first portion and the second portion, wherein the first portion, second portion, and separation generally extend parallel to the longitudinal centerline.

9. The sanitary napkin of claim 8, wherein the separation is less than 2 times a caliper of at least one of the first portion and the second portion.

10. The sanitary napkin of claim 1, wherein a second region first absorbent layer width is less than a second region second absorbent layer width.

11. The sanitary napkin of claim 1, comprising at least one of a distribution layer and a superabsorbent layer.

12. The sanitary napkin of claim 1, wherein the first absorbent layer comprises a first distribution layer and a first superabsorbent layer and the second absorbent layer comprises a second distribution layer and a second superabsorbent layer.

13. The sanitary napkin of claim 12, wherein the first distribution layer is joined to the second distribution layer.

14. The sanitary napkin of claim 12, wherein the first distribution layer is joined to the second superabsorbent layer.

15. The sanitary napkin of claim 1, wherein the first absorbent layer comprises a first end edge and an opposing second end edge, wherein the first end edge of the first absorbent layer is convex and the second end edge of the first absorbent layer is concave.

16. The sanitary napkin of claim 1, wherein the second absorbent layer first end edge is concave and the second absorbent layer second end edge is convex.

17. A sanitary napkin having a longitudinal centerline and a lateral centerline generally perpendicular to the longitudinal centerline, the sanitary napkin comprising:

a topsheet;

a backsheet;

a first end region, an opposing second end region and an intermediate region disposed between the first end region and the second end region;

a first absorbent layer disposed between the topsheet and the backsheet, the first absorbent layer having a first end region first absorbent layer width, an intermediate region first absorbent layer width measured along the lateral centerline, and a second end region first absorbent layer width;

a second absorbent layer disposed between the first absorbent layer and the backsheet, the second absorbent layer having a first end region second absorbent layer width, an intermediate region second absorbent layer width measured along the lateral centerline, and a second end region second absorbent layer width, wherein the respective widths have the following relationships:

the first end region first absorbent layer width is greater than the second end region first absorbent layer width, and the second end region first absorbent layer width is greater than the intermediate region first absorbent layer width, and the first end region second absorbent layer width is greater than the second end region second absorbent layer width, and the second end region second absorbent layer width is greater than the intermediate region second absorbent layer width, wherein the first absorbent layer comprises a first end edge and an opposing second end edge, wherein the second absorbent layer comprises a first end edge and an opposing second end edge, and wherein the first end edge of the first absorbent layer is coterminous with the first end edge of the second absorbent layer and the second end edge of the first absorbent layer is coterminous with the second end edge of the second absorbent layer.

18. The sanitary napkin of claim 17, wherein at least one of the first end edge and the second end edge of the first absorbent layer is substantially flat.

19. The sanitary napkin of claim 17, wherein at least one of the first end edge and the second end edge of the second absorbent layer is substantially flat.

20. The sanitary napkin of claim 17, wherein the second absorbent layer extends outboard of the first absorbent layer in at least one of the first end region, the second end region, and the intermediate region.

* * * * *